(12) United States Patent
Salituro et al.

(10) Patent No.: US 8,501,953 B2
(45) Date of Patent: Aug. 6, 2013

(54) PKM2 MODULATORS FOR USE IN THE TREATMENT OF CANCER

(75) Inventors: Francesco G. Salituro, Marlborough, MA (US); Jeffrey O. Saunders, Lincoln, MA (US)

(73) Assignee: Agios Pharmaceuticals, Inc, Cambridge, MA (US)

( * ) Notice: Subject to any disclaimer, the term of this patent is extended or adjusted under 35 U.S.C. 154(b) by 0 days.

(21) Appl. No.: 13/289,551

(22) Filed: Nov. 4, 2011

(65) Prior Publication Data

US 2012/0122849 A1 May 17, 2012

Related U.S. Application Data

(63) Continuation of application No. PCT/US2010/033610, filed on May 4, 2010.

(60) Provisional application No. 61/175,217, filed on May 4, 2009.

(51) Int. Cl.
*C07D 277/68* (2006.01)
*C07D 263/58* (2006.01)

(52) U.S. Cl.
USPC .......................................... 548/172; 548/221

(58) Field of Classification Search
USPC ............ 514/218, 375, 367, 441, 338, 254.02, 514/314; 548/221, 172; 549/33; 546/280.7, 546/171; 544/368; 540/575
See application file for complete search history.

(56) References Cited

U.S. PATENT DOCUMENTS

| | | | |
|---|---|---|---|
| 3,046,122 A * | 7/1962 | Sus ................................ | 430/193 |
| 3,097,210 A | 7/1963 | Bicking | |
| 3,998,828 A | 12/1976 | Wiedermann | |
| 4,235,871 A | 11/1980 | Papahadjopoulos et al. | |
| 4,315,940 A | 2/1982 | Hitzel et al. | |
| 4,501,728 A | 2/1985 | Geho et al. | |
| 4,593,102 A | 6/1986 | Shanklin, Jr. | |
| 4,775,762 A | 10/1988 | Knox et al. | |
| 4,837,028 A | 6/1989 | Allen | |
| 4,889,553 A | 12/1989 | Rowson et al. | |
| 5,019,369 A | 5/1991 | Presant et al. | |
| 5,122,530 A | 6/1992 | Tomioka et al. | |
| 5,180,732 A | 1/1993 | Tomioka et al. | |
| 5,220,028 A | 6/1993 | Iwasawa et al. | |
| 5,252,590 A | 10/1993 | Tomioka et al. | |
| 5,556,866 A | 9/1996 | Aga et al. | |
| 5,843,485 A | 12/1998 | Fernandez et al. | |
| 5,962,490 A | 10/1999 | Chan et al. | |
| 6,020,357 A | 2/2000 | Pinto et al. | |
| 6,106,849 A | 8/2000 | Malkan et al. | |
| 6,150,356 A | 11/2000 | Lloyd et al. | |
| 6,172,005 B1 | 1/2001 | Selby | |
| 6,265,588 B1 | 7/2001 | Mullner et al. | |
| 6,511,977 B1 | 1/2003 | Lloyd et al. | |
| 6,818,631 B1 | 11/2004 | Nakagawa et al. | |
| 7,288,554 B2 | 10/2007 | Finkelstein et al. | |
| 7,572,913 B2 | 8/2009 | McKerracher et al. | |
| 7,863,444 B2 | 1/2011 | Calderwood et al. | |
| 8,058,313 B2 | 11/2011 | Reddy et al. | |
| 2003/0082877 A1 | 5/2003 | Ootsuka et al. | |
| 2003/0095958 A1 | 5/2003 | Bhisetti et al. | |
| 2003/0106381 A1 | 6/2003 | Krouth et al. | |
| 2003/0158232 A1 | 8/2003 | Cheng et al. | |
| 2003/0187001 A1 | 10/2003 | Calderwood et al. | |
| 2003/0207882 A1 | 11/2003 | Stocker et al. | |
| 2004/0048283 A1 | 3/2004 | Pau et al. | |
| 2004/0152648 A1 | 8/2004 | Ullrich et al. | |
| 2004/0198979 A1 | 10/2004 | Dhanak et al. | |
| 2004/0235755 A1 | 11/2004 | Eigenbrodt et al. | |
| 2005/0176675 A1 | 8/2005 | Gorny | |
| 2007/0032418 A1 | 2/2007 | Shapiro et al. | |
| 2007/0127505 A1 | 6/2007 | Laurila et al. | |
| 2007/0280918 A1 | 12/2007 | Schwartz et al. | |
| 2008/0004269 A1 | 1/2008 | Xu et al. | |
| 2008/0021116 A1 | 1/2008 | Ullrich et al. | |
| 2008/0044833 A1 | 2/2008 | Connors | |
| 2008/0051414 A1 | 2/2008 | Hurley et al. | |
| 2009/0048227 A1 | 2/2009 | Chakravarty et al. | |
| 2009/0054453 A1 | 2/2009 | Alcaraz et al. | |
| 2009/0163545 A1 | 6/2009 | Goldfarb | |
| 2009/0270454 A1 | 10/2009 | Weingarten et al. | |
| 2010/0105657 A1 | 4/2010 | Nordvall et al. | |
| 2010/0179150 A1 | 7/2010 | Basarab et al. | |
| 2011/0046083 A1 | 2/2011 | Cantley et al. | |
| 2011/0224252 A1 | 9/2011 | Dumeunier et al. | |
| 2011/0312931 A1 | 12/2011 | Cioffi et al. | |

FOREIGN PATENT DOCUMENTS

| | | |
|---|---|---|
| DE | 19841985 A1 | 3/2000 |
| EP | 1586558 A2 | 10/2005 |
| GB | 1274436 A | 5/1972 |
| WO | 8501289 A1 | 3/1985 |

(Continued)

OTHER PUBLICATIONS

Kharalkar et al., "Identification of Novel Allosteric Regulators of Human-Erythrocyte Pyruvate Kinase," Chem Biodivers. 4: 2603-2617 (2007).

Klapars et al., "A General and Efficient Copper Catalyst for the Amidation of Aryl Halides and the N-Arylation of Nitrogen Heterocycles," J. Am. Chem. Soc., 123 (31), 7727-7729 (2001).

Kumar et al., "In vivo factors influencing tumour M2-pyruvate kinase level in human pancreatic cancer cell lines." Tumour Biol.;31(2):69-77 (2010).

Lee et al., "An Efficient Synthesis of 2,8-Diazabicyclo[4.3.0]-Nonane Derivatives Via Intramolecular Cyclization Reaction," Synth. Comm., 25 (23), 3741-3746 (1995).

Lee, "Consolidation Effect of Phenylalanine-administration of Antitumor Activity of a 5 Fluorouracil," Med. J. Kagoshima Univ. 37(3-4): 285-308 (1985).

(Continued)

*Primary Examiner* — Kristin Bianchi
(74) *Attorney, Agent, or Firm* — Lando & Anastasi LLP

(57) ABSTRACT

Compounds that modulate pyruvate kinase M2 (PKM2) are described herein. Also described herein are pharmaceutical compositions comprising the compounds, and methods of using the compounds in the treatment of cancer.

18 Claims, No Drawings

FOREIGN PATENT DOCUMENTS

| | | |
|---|---|---|
| WO | 93/13072 A1 | 7/1993 |
| WO | 98/03350 A1 | 1/1998 |
| WO | 00/53596 A2 | 9/2000 |
| WO | 02/072077 A2 | 9/2002 |
| WO | 02/095063 A1 | 11/2002 |
| WO | 03/062235 A1 | 7/2003 |
| WO | 03/073999 A2 | 9/2003 |
| WO | 2004/004730 A2 | 1/2004 |
| WO | 2004/037251 A1 | 5/2004 |
| WO | 2004/110375 A2 | 12/2004 |
| WO | 2005/117591 A2 | 12/2005 |
| WO | 2006/004195 A1 | 1/2006 |
| WO | 2006/016062 A1 | 2/2006 |
| WO | 2006/122546 A1 | 11/2006 |
| WO | 2007023186 A1 | 3/2007 |
| WO | 2007/127505 A2 | 11/2007 |
| WO | 2008/019139 A2 | 2/2008 |
| WO | 2008/026658 A1 | 3/2008 |
| WO | 2009/025781 A1 | 2/2009 |
| WO | 2010/042867 A2 | 4/2010 |
| WO | 2010105243 A1 | 9/2010 |
| WO | 2011002817 A1 | 1/2011 |

OTHER PUBLICATIONS

Lee, et al., "Pyruvate kinase isozyme type M2 (PKM2) interacts and cooperates with Oct-4 in regulating transcription" International J. Biochem. & Cell Biol., vol. 40, # 5,2008, 1043-1054.

Li et al., "Quantitative proteome analysis of multidrug resistance in human ovarian cancer cell line." J Cell Biochem.;109(4):625-33 (2010).

Li et al., "Screening and identification of interactive proteins of SH2D4A." Yi Chuan.;32(7):712-8 (2010).

Mass, R. D., "The HER receptor family: a rich target for therapeutic development", Int. J. Radiation Oncology Bio. Phys. vol. 58(3): 932-940, 2004.

Oeda, "On some 2,5-Dialikl-piperazines," Bull. Chem. Soc., 13, 465-470 (1938).

Park, "Prevention of type 2 diabetes mellitus from the viewpoint of genetics." Diabetes Research and Clinical Practice 2004; 66S: S33-S35.

Paudler et al., "3,7-Disubstituted octahydro-1,5-diazocines. Their conversion into tetrahydro-1 ,5-diazocines and into ring-contracted products," J. Org. Chern., 32 (8), 2425-2430 (1967).

Pollard et al., "Some Amides of Piperazines," J. Am. Chem. Soc., 75 (2), 491 (1953).

Pujol, et. al., "Is there a case for cisplatin in the treatment of smallcell lung cancer? A meta-analysis of randomized trials of a cisplatin-containing regimen versus a regimen without this alkylating agent" British Journal of Cancer, Cancer Research Campaign, vol. 83, issue 1, pp. 8-15, 2000.

Remington's, "Structure Activity Relationship and Drug Design," Pharmaceutical Sciences, pp. 420-425p. 420-425, 1980.

Rich, et. al., "Development of novel targeted therapies in the treatment of malignant glioma" Nature Rev. Drug Disc., Nature Publishing Group, vol. 3, pp. 430-446, 2004.

Root et al., "Genome-Scale Loss-of-Function Screening with a Lentiviral RNAi Library," Nat Methods 3: 715-719 (2006).

Ruan et al., "HSP60, a protein downregulated by IGFBP7 in colorectal carcinoma." J Exp Clin Cancer Res.;29:41 (2010).

Sabatine et al., "Metabolomic Identification of Novel Biomarkers of Myocardial Ischemia," Circulation 112: 3868-3875 (2005).

Schneider, et. al., "Tumor M2-pyruvate kinase in the follow-up of inoperable lung cancer patients: a pilot study." Cancer Letters, Elsevier, vol. 193, pp. 91-98, 2003.

Schroth et al., "RingschluBreaktion von Diacetylen mit Diaminen: Eine Ciniache von 2,3-Dihydro-1 ,4-diazepinen," Zeitschritt Fur Chemie., 6 (4), 143 (1969).

Seibel et al., "Synthesis and evaluation of B-lactams (piperazones) as elastase inhibitors," Bioorg. Med. Chern. Ltrs., 13 (3),387-389 (2003).

Shi, et al., "Silencing of pkm2 increases the efficacy of docetaxel in human lung cancer xenografts in mice." Cancer Science, vol. 101, # 6, 1447-1453, Jun. 2010.

Stewart et al., "Piperazines. I. Derivatives of Piperazine-1-Carboxylic and -1,4-Dicarboxylic Acid,", J. Org. Chern., 18 (1),1478-1483 (1953).

Surh, "Cancer Chemoprevention with Dietary Phytochemicals", Nature Reviews Cancer, Nature Publishing Group, vol. 3, p. 768-780, 2003.

Szoka et al., "Comparative properties and methods of preparation of lipid vesicles (liposomes )," Ann. Rev. Biophys. Bioeng., 9, 467-508 (1980).

Tawaka, et al., Caplus an 1998:794998.

Uozumi et al., "Catalytic asymmetric construction of morpholines and piperazines by palladium-catalyzed tandem allylic substitution reactions," J. Org. Chem., 58 (24),6826-6832 (1993).

Vander Heiden et al., "Growth Factors Can Influence Cell Growth and Survival Through Effects on Glucose Metabolism," Mol Cell Bioi. 21: 5899-5912 (2001).

Vander Heiden et al., "Identification of Small Molecule Inhibitors of Pyruvate Kinase M2," Biochemical Pharmacology. 79(8): 1118-1124 (2010).

Villen et al., "Large-Scale Phosphorylation Analysis of Mouse Liver," Proc Nat! Acad Sci USA 104: 1488-1493 (2007).

Written Opinion of the International Searching Authority for PCT/US2008/009828, dated Dec. 5, 2008.

Yamada and Noguchi, "Nutrient and Hormonal Regulation of Pyruvate Kinase Gene Expression," Biochem J. 337: 1-11 (1999).

Yar et al., "An Annulation Reaction for the Synthesis of Morpholines, Thiomorpholines, and Piperazines from !3-Heteroatom Amino Compounds and Vinyl Sulfonium Salts," Angewandte Chemie., 47 (20),3784-3786 (2008).

Adveenko, et al., "Thiocyanation of N-arylsulfonyl-, N-aroyl-, and N-[(N-arylsulfonyl)benzimidoyl]-1,4-benzoquinone imines" Russian Journal of Organic Chemistry, vol. 45, No. 3 (2009), 408-416.

Baxter I et al: "Preparation and some reactions of 6-arylsulphonimidobenzoxazol-2(3H)-one" Journal of the Chemical Society, Section C: Organic Chemistry, Chemical Society. Letchworth, GB LNKD-DOI:10.1039/J39700000850, Jan. 1, 1970, pp. 850-853.

Behun et al., "The Chemistry of Pyrazine and Its Derivatives. IV. The Alkylation and Arylation of Methylpyrazine," J Org. Chern., 26 (9),3379-3382 (1961).

Benesch et al., "The clinicopathological and prognostic relevance of pyruvate kinase M2 and pAkt expression in breast cancer." Anticancer Res.;30(5):1689-94 (2010).

Berger, et. al., "Treatment of Pancreatic Cancer: Challenge of the Facts" World J. Surg., Societe Internationale de Chirurgie, vol. 27, pp. 1075-1083, 2003.

Bonuccelli et al., "The reverse Warburg effect: Glycolysis inhibitors prevent the tumor promoting effects of caveolin-1 deficient cancer associated fibroblasts." Cell Cycle.;9(10) (2010).

Boxer, et al., "Evaluation of Substituted N,N?-Diarylsulfonamides as Activators of the Tumor Cell Specific M2 Isoform of Pyruvate Kinase", J Med Chem. Feb. 11, 2010; 53(3): 1048.

Boxer, et al., "Identification of activators for the M2 isoform of human pyruvate kinase Version 3", Sep. 2009, Probe Reports from the NIH Molecular Libraries Program [Internet]. Bethesda (MD): National Center for Biotechnology Information (US).

Budinger et al., "Cellular Energy Utilization and Supply During Hypoxia in Embryonic Cardiac Myocytes," Am J Physiol. 270: L44-53 (1996).

Buschow et al., "MHC class II-associated proteins in B-cell exosomes and potential functional implications for exosome biogenesis." Immunol Cell Biol. (2010).

Cecil Textbook of Medicine, edited by Bennet, J.C., and Plum F., 20th edition, vol. 1, 1004-1010, 1996.

Chabner, et. al., "Chemotherapy and the war on cancer", Nature Rev. Cancer, Nature Publishing Group, vol. 5, pp. 65-72, 2005.

Chan et al., "Synthesis and characterization of poly(amide sulfonamide)s (PASAs)," J Polymer. Sci., 33 (15), 2525-2531 (1995).

Christofk et al., "pyruvate Kinase M2 is a Phosphotyrosine-Binding Protein," Nature 452: 181-186 (2008).

Christofk et al., "The M2 Splice Isoform of Pyruvate Kinase is Important for Cancer Metabolism and Tumour Growth," Nature 452: 230-233 (2008).

Clement, et. al., "Production of Intracellular Superoxide Mediates Dithiothreitol-Dependent Inhibition of Apoptotic Cell Death" Antioxidants and Redox Signaling, Mary Ann Liebert, vol. 7, issues 3-4, pp. 456-464, 2005.

Cohen et al., "The development and therapeutic potential of protein kinase inhibitors", Current Opinion in Chemical Biology, 3,459-465, 1999.

Cuzick, et. al., "Overview of the main outcomes in breast-cancer prevention trials" The Lancet, The Lancet Publishing Group, vol. 361, pp. 296-300, 2003.

Database Chemcats, Chemical Abstracts Service, Columbus, OH, US "Bionet Screening Compounds" Key Organics Ltd., Camelford, Cornwall (2001).

Dermer et al., "Another Anniversary for the War on Cancer", Bio/Technology, 1994, 12:320.

Dombrauckas, et al., Structural Basis for Tumor Pyruvate Kinasa M2 Allosteric Regulation and Catalysis, Biochemistry, vol. 44, p. 9717-9429 (2005).

Eigenbrodt et al., "Double Role for Pyruvate Kinase Type M2 in the Expansion of Phosphometabolite Pools Found in Tumor Cells," Crit Rev Oncog. 3: 91-115 (1992). (Abstract only).

Engelman et al., "Allelic Dilution Obscures Detection of a Biologically Significant Resistance Mutation in EGFR-Amplified Lung Cancer," J Clin Invest. 116: 2695-2706 (2006).

Eswaran et al., "Crystal Structures and Inhibitor Identification for PTPN5, PTPRR and PTPN7: A Family of Human MAPK-Specific Protein Tyrosine Phosphatases," Biochem J. 395: 483-491 (2006).

European Patent Office Communication (European Application No. 07836571.5), dated Oct. 18, 2010.

Fabbro et al. "Protein kinases as targets for anticancer agents: from inhibitors to useful drugs." Pharmacology & Therapeutics 93, 79-98, 2002.

Freshney et al.,Culture of Animal Cells, a Manual of Basic Technique, Alan R. Liss, Inc., 1983, New York, p. 4.

Friedman et al., "Leptin and the regulation of body weight in mammals" Nature. vol. 395, 1996.

Golub et al., "Molecular Classification of Cancer: Class Discovery and Class Prediction by Gene Expression Monitoring", Science, 286, 531-537, 1999.

Gupta et al., "Dominant negative mutations affect oligomerisation of human pyruvate kinase M2 isozyme and promote cellular growth and polyploidy." J Biol Chem. (2010).

Hitosugi T et al: "Tyrosine Phosphorylation Inhibits PKM2 to Promote the Warburg Effect and Tumor Growth" Science Signaling, American Association for the Advancement of Science, US LNKD-DOI:10.1126/SCISIGNAL.2000431, vol. 2, No. 97, Nov. 17, 2009, pp. RA73-1.

Hitosugi, et al., "Tyrosine Phosphorylation Inhibits PKM2 to Promote the Warburg Effect and Tumor Growth" Sci. Signal., Nov. 17, 2009, vol. 2, Issue 97, p. ra73.

Hulleman, et al., "Pyruvate kinase M2 and prednisolone resistance in acute lymphoblastic leukemia." Haematologica. Sep. 2009; 94(9): 1322-1324.

Inglese et al., "Quantitative high-throughput screening: A titration-based approach that efficiently identifies biological activities in large chemical libraries," ProC. Nat!. Acad. Sci., 103 (31), 11473-11478 (2006).

International Preliminary Report on patentability for International Application No. PCT/US2007/017519, issued Feb. 10, 2009.

International Preliminary Report on Patentability for PCT/US2008/009828, dated Feb. 16, 2010.

International Preliminary Report on Patentability, Application No. PCT/US2009/060237, dated Apr. 12, 2011.

International Search Report & Written Opinion for PCT/US10/030139 dated Dec. 10, 2010.

International Search Report & Written Opinion for PCT/US10/40485 dated Aug. 11, 2010.

International Search Report and the Written Opinion of the International Search Authority (PCT/US07/17519), mailed Jul. 8, 2008.

International Search Report dated Mar. 5, 2012 for related international application No. PCT/US2011/067752.

International Search Report for PC/US10/40486 dated Sep. 1, 2010.

International Search Report for PCT/US2008/009828, dated Dec. 5, 2008.

International Search Report for PCT/US2010/033610 dated Jul. 22, 2010.

International Search Report, Application No. PCT/US2009/060237, dated Jun. 16, 2010.

International Search Report, Application No. PCT/US2011/033852, dated Aug. 3, 2011.

Jiang et al., "Evaluation of thieno[3,2-b]pyrrole[3,2-d]pyridazinones as activators of the tumor cell specific M2 isoform of pyruvate kinase." Bioorg. Med. Chern. Lett., 20 (11), 3387-3393 (2010).

Joshi et al., "Age-related faecal calprotectin, lactoferrin and tumour M2-PK concentrations in healthy volunteers." Ann Clin Biochem. ;47(Pt 3):259-63 (2010).

Jurica et al., "The Allosteric Regulation of Pyruvate Kinase by Fructose-1,6-Bisphosphate," Structure 6: 195-210 (1998).

Kao et al., "A Small-Molecule Inhibitor of the Ribonucleolytic Activity of Human Angiogenin That Possesses Antitumor Activity," Proc. Nat!. Acad. Sci. USA, 99(15): 10066-10071 (2002).

* cited by examiner

PKM2 MODULATORS FOR USE IN THE TREATMENT OF CANCER

CLAIM OF PRIORITY

The present application is a continuation of International Application No. PCT/US2010/033610, filed May 4, 2010, published as International Publication No. WO 2010/129596 on Nov. 11, 2010, which claims priority from U.S. Ser. No. 61/175,217, filed May 4, 2009, each of which is incorporated herein by reference in its entirety.

BACKGROUND OF INVENTION

Cancer cells rely primarily on glycolysis to generate cellular energy and biochemical intermediates for biosynthesis of lipids and nucleotides, while the majority of "normal" cells in adult tissues utilize aerobic respiration. This fundamental difference in cellular metabolism between cancer cells and normal cells, termed the Warburg Effect, has been exploited for diagnostic purposes, but has not yet been exploited for therapeutic benefit.

Pyruvate kinase (PK) is a metabolic enzyme that converts phosphoenolpyruvate to pyruvate during glycolysis. Four PK isoforms exist in mammals: the L and R isoforms are expressed in liver and red blood cells, the M1 isoform is expressed in most adult tissues, and the M2 isoform is a splice variant of M1 expressed during embryonic development. All tumor cells exclusively express the embryonic M2 isoform. A well-known difference between the M1 and M2 isoforms of PK is that M2 is a low-activity enzyme that relies on allosteric activation by the upstream glycolytic intermediate, fructose-1,6-bisphosphate (FBP), whereas M1 is a constitutively active enzyme.

All tumor cells exclusively express the embryonic M2 isoform of pyruvate kinase, suggesting PKM2 as a potential target for cancer therapy. PKM2 is also expressed in adipose tissue and activated T-cells. Thus, the modulation (e.g., inhibition or activation) of PKM2 may be effective in the treatment of, e.g., obesity, diabetes, autoimmune conditions, and proliferation-dependent diseases, e.g., benign prostatic hyperplasia (BPH). Current modulators (e.g., inhibitors) of pyruvate kinase are not selective, making it difficult to treat disease related to pyruvate kinase function.

Furthermore, phosphotyrosine peptide binding to PKM2 leads to a dissociation of FBP from PKM2 and conformational changes of PKM2 from an active, tetrameric form to an inactive form. Compounds that bind to PKM2 and lock the enzyme in the active confirmation will lead to the loss of allosteric control of PKM2 needed for shunting biochemical intermediates from glycolysis into biosynthesis of nucleotides and lipids. Thus, the activation of PKM2 can also inhibit the growth and proliferation of cancer cells, activated immune cells, and fat cells.

There is a continuing need for novel treatments of diseases such as cancer, diabetes, obesity, autoimmune conditions, proliferation-dependent diseases (e.g., BPH), and other diseases related to the function of pyruvate kinase (e.g., PKM2).

SUMMARY OF INVENTION

Described herein are compounds that modulate pyruvate kinase M2 (PKM2) and pharmaceutically acceptable salts, solvates, and hydrates thereof. For example, a compound described herein may activate or inhibit PKM2. This invention also provides compositions and pharmaceutical kits comprising a compound of this invention and the use of such compositions and kits in methods of treating diseases and conditions that are related to pyruvate kinase function (e.g., PKM2 function), including, e.g., cancer, diabetes, obesity, autoimmune disorders, and benign prostatic hyperplasia (BPH).

In one aspect, the invention features a compound of formula (I):

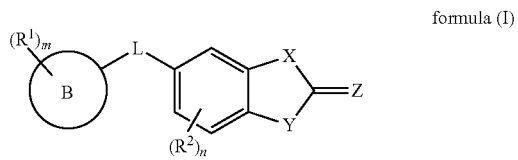

formula (I)

wherein:

m is an integer from 0 to 5;

each $R^1$ is independently selected from $C_1$-$C_6$ alkyl, $C_1$-$C_6$ alkoxy, $C_1$-$C_6$ haloalkyl, $C_{1-6}$ haloalkoxy, halo, acetyl, —$NO_2$, aryl, aralkyl, heteroaryl, —$SO_2$-aryl, —C(O)—$NR^b$-aryl, —C(O)-aralkyl, —C(O)—$C_{1-6}$ alkoxy, —$NR^b$—$SO_2$-aryl, wherein each aryl, aralkyl and heteroaryl group is optionally substituted with 0-3 occurrences of $R^c$ and wherein two $R^1$ groups taken together with the carbon atoms to which they are attached form a heterocyclyl ring;

n is an integer from 1 to 3;

each $R^2$ is independently selected from $C_1$-$C_6$ alkyl and halo;

B is aryl, monocyclic heteroaryl, cycloalkyl, heterocyclyl, $C_{1-6}$ aralkyl, or $C_{1-6}$ heteroaralkyl;

L is a linker selected from —$SO_2$—, —$SO_2NR^a$— and —$NR^aSO_2$—;

each $R^a$ is independently selected from hydrogen and $C_1$-$C_6$ alkyl;

X and Y are each independently selected from O, S, $NR^b$ and $CH_2$, wherein at least one of X and Y is O or S;

Z is O or S;

each $R^b$ is independently selected from hydrogen, $C_{1-6}$ aralkyl, and $C_1$-$C_6$ alkyl substituted with 0-1 occurrences of $R^c$; and $R^c$ is independently selected from $C_{1-6}$ alkyl, $C_{1-6}$ alkoxy, $C_{1-6}$ haloalkyl, halo, $NR^dR^d$, and heterocyclyl and wherein two $R^c$ groups taken together with the carbon atoms to which they are attached form a heterocyclyl ring; and $R^d$ is independently selected from H and $C_{1-6}$ alkyl.

In some embodiments, each $R^1$ is independently selected from $C_1$-$C_6$ alkyl, $C_1$-$C_6$ alkoxy, $C_1$-$C_6$ haloalkyl, halo, acetyl and —$NO_2$;

In some embodiments, each $R^b$ is independently selected from hydrogen and $C_1$-$C_6$ alkyl.

In some embodiments, B is a monocyclic heteroaryl, cycloalkyl, heterocyclyl, $C_{1-6}$ aralkyl, or $C_{1-6}$ heteroaralkyl.

In some embodiments, B is a monocyclic heterocyclyl (e.g., a 6-membered monocyclic heterocyclyl). In some embodiments, B is a 6-membered nitrogen containing monocyclic heterocyclyl (e.g., piperazinyl). In some embodiments, B is unsubstituted piperazinyl. In some embodiments, B is piperazinyl substituted with an $R^1$. In some embodiments, B is a 7-membered nitrogen containing monocyclic heterocyclyl (e.g., 1,4-diazepam). In some embodiments, B is unsubstituted 1,4-diazepam. In some embodiments, B is 1,4-diazepam substituted with an $R^1$.

In some embodiments, B is a monocyclic heteroaryl. In some embodiments, B is a 5-membered monocyclic heteroaryl (e.g., thiophenyl). In some embodiments, B is a 6-membered monocyclic heteroaryl, e.g., a 6-membered nitrogen-containing monocyclic heteroaryl (e.g., pyridyl). In some embodiments, B is pyridyl substituted with 2 $R^1$. In some embodiments, one $R^1$ is halo and the other is haloalkyl. In some embodiments, one $R^1$ is chloro and the other is trifluoromethyl.

In some embodiments, B is monocyclic aryl (e.g., phenyl). In some embodiments, B is unsubstituted phenyl. In some embodiments, B is phenyl substituted with one $R^1$. In some embodiments, B is phenyl substituted with two $R^1$.

In some embodiments, n is 1. In some embodiments, $R^2$ is $C_1$-$C_6$ alkyl (e.g., methyl). In some embodiments, $R^2$ is halo (e.g., fluoro, chloro or bromo).

In some embodiments, L is a linker selected from —$SO_2$—. In some embodiments, L is a linker selected from —$SO_2NR^a$— and —$NR^aSO_2$—. In some embodiments, L is —$SO_2NR^a$—. In some embodiments, $R^a$ is hydrogen. In some embodiments, $R^a$ is $C_1$-$C_6$ alkyl (e.g., methyl, ethyl or isopropyl). In some embodiments, L is —$NR^aSO_2$—. In some embodiments, $R^a$ is hydrogen. In some embodiments, $R^a$ is $C_1$-$C_6$ alkyl (e.g., methyl, ethyl or isopropyl).

In some embodiments, X is S. In some embodiments, X is O. In some embodiments, X is $NR^b$. In some embodiments, $R^b$ is hydrogen. In some embodiments, $R^b$ is $C_1$-$C_6$ alkyl (e.g., methyl, ethyl, isopropyl or sec-butyl). In some embodiments, Y is S. In some embodiments, Y is O. In some embodiments, Y is $NR^b$. In some embodiments, $R^b$ is hydrogen. In some embodiments, $R^b$ is $C_1$-$C_6$ alkyl (e.g., methyl, ethyl, isopropyl or sec-butyl).

In some embodiments, one of X and Y is O and the other is S. In some embodiments, one of X and Y is O and the other is $NR^b$. In some embodiments, $R^b$ is hydrogen. In some embodiments, $R^b$ is $C_1$-$C_6$ alkyl (e.g., methyl, ethyl, isopropyl or sec-butyl). In some embodiments, one of X and Y is S and the other is $NR^b$. In some embodiments, $R^b$ is hydrogen. In some embodiments, $R^b$ is $C_1$-$C_6$ alkyl (e.g., methyl, ethyl, isopropyl or sec-butyl).

In some embodiments, Z is O.

In some embodiments, the compound of formula (I) is represented by the following formula:

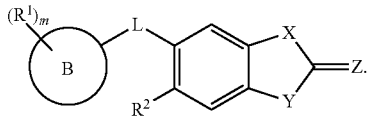

In one aspect, the invention features a compound of formula (II):

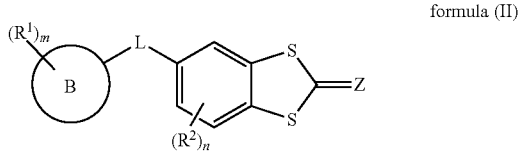

formula (II)

wherein:

m is an integer from 0 to 5;

each $R^1$ is independently selected from $C_1$-$C_6$ alkyl, $C_1$-$C_6$ alkoxy, $C_{1-6}$ haloalkyl, $C_{1-6}$ haloalkoxy, halo, acetyl, —$NO_2$, aryl, aralkyl, heteroaryl, —$SO_2$-aryl, —$C(O)$—$NR^b$-aryl, —$C(O)$-aralkyl, —$C(O)$—$C_{1-6}$ alkoxy, —$NR^b$—$SO_2$-aryl, wherein each aryl, aralkyl and heteroaryl group is optionally substituted with 0-3 occurrences of $R^c$ and wherein two $R^1$ groups taken together with the carbon atoms to which they are attached form a heterocyclyl ring;

n is an integer from 1 to 3;

each $R^2$ is independently selected from $C_1$-$C_6$ alkyl and halo;

B is aryl, monocyclic heteroaryl, cycloalkyl, heterocyclyl, $C_{1-6}$ aralkyl, or $C_{1-6}$ heteroaralkyl;

L is a linker selected from —$SO_2$—, —$SO_2NR^a$— and —$NR^aSO_2$—;

each $R^a$ is independently selected from hydrogen and $C_1$-$C_6$ alkyl;

Z is O or S;

each $R^b$ is independently selected from hydrogen, $C_{1-6}$ aralkyl, and $C_1$-$C_6$ alkyl substituted with 0-1 occurrences of $R^c$; and $R^c$ is independently selected from $C_{1-6}$ alkyl, $C_{1-6}$ alkoxy, $C_{1-6}$ haloalkyl, halo, $NR^dR^d$, and heterocyclyl and wherein two $R^c$ groups taken together with the carbon atoms to which they are attached form a heterocyclyl ring; and $R^d$ is independently selected from H and $C_{1-6}$ alkyl.

In some embodiments, each $R^1$ is independently selected from $C_1$-$C_6$ alkyl, $C_1$-$C_6$ alkoxy, $C_1$-$C_6$ haloalkyl, halo, acetyl and —$NO_2$.

In some embodiments, L is a linker selected from —$SO_2NR^a$— and —$NR^aSO_2$—.

In some embodiments, each $R^b$ is independently selected from hydrogen and $C_1$-$C_6$ alkyl.

In some embodiments, B is a monocyclic heteroaryl, cycloalkyl, heterocyclyl, $C_{1-6}$ aralkyl, or $C_{1-6}$ heteroaralkyl.

In some embodiments, B is a monocyclic heterocyclyl (e.g., a 6-membered monocyclic heterocyclyl). In some embodiments, B is a 6-membered nitrogen containing monocyclic heterocyclyl (e.g., piperazinyl). In some embodiments, B is unsubstituted piperazinyl. In some embodiments, B is piperazinyl substituted with an $R^1$. In some embodiments, B is a 7-membered nitrogen containing monocyclic heterocyclyl (e.g., 1,4-diazepam). In some embodiments, B is unsubstituted 1,4-diazepam. In some embodiments, B is 1,4-diazepam substituted with an $R^1$.

In some embodiments, B is a monocyclic heteroaryl. In some embodiments, B is a 5-membered monocyclic heteroaryl (e.g., thiophenyl). In some embodiments, B is a 6-membered monocyclic heteroaryl, e.g., a 6-membered nitrogen-containing monocyclic heteroaryl (e.g., pyridyl). In some embodiments, B is pyridyl substituted with 2 $R^1$. In some embodiments, one $R^1$ is halo and the other is haloalkyl. In some embodiments, one $R^1$ is chloro and the other is trifluoromethyl.

In some embodiments, B is monocyclic aryl (e.g., phenyl). In some embodiments, B is unsubstituted phenyl. In some embodiments, B is phenyl substituted with one $R^1$. In some embodiments, $R^1$ is halo (e.g., fluoro, chloro or bromo). In some embodiments, $R^1$ is $C_1$-$C_6$ alkyl (e.g., methyl). In some embodiments, $R^1$ is $C_1$-$C_6$ alkoxy (e.g., methoxy). In some embodiments, $R^1$ is acetyl. In some embodiments, $R^1$ is —$NO_2$.

In some embodiments, B is phenyl substituted with two $R^1$. In some embodiments, one $R^1$ is halo (e.g., fluoro or chloro) and the other is $C_1$-$C_6$ alkoxy (e.g., methoxy).

In some embodiments, both $R^1$ are halo (e.g., fluoro or chloro). In some embodiments, one $R^1$ is $C_1$-$C_6$ alkyl (e.g., methyl) and the other is $C_1$-$C_6$ alkoxy (e.g., methoxy). In some embodiments, both $R^1$ are $C_1$-$C_6$ alkoxy (e.g., methoxy).

In some embodiments, B is a 5-membered monocyclic heteroaryl (e.g., thiophenyl). In some embodiments, B is a 6-membered monocyclic heteroaryl, e.g., a 6-membered nitrogen-containing monocyclic heteroaryl (e.g., pyridyl). In some embodiments, B is pyridyl substituted with 2 $R^1$. In some embodiments, one $R^1$ is halo and the other is haloalkyl. In some embodiments, one $R^1$ is chloro and the other is trifluoromethyl. In some embodiments, B is cycloalkyl (e.g., cyclohexyl).

In some embodiments, n is 1. In some embodiments, $R^2$ is $C_1$-$C_6$ alkyl (e.g., methyl). In some embodiments, $R^2$ is halo (e.g., fluoro, chloro or bromo).

In some embodiments, L is —$SO_2$—. In some embodiments, L is —$SO_2NR^a$—. In some embodiments, $R^a$ is hydrogen. In some embodiments, $R^a$ is $C_1$-$C_6$ alkyl (e.g., methyl, ethyl or isopropyl). In some embodiments, L is —$NR^aSO_2$—. In some embodiments, $R^a$ is hydrogen. In some embodiments, $R^a$ is $C_1$-$C_6$ alkyl (e.g., methyl, ethyl or isopropyl).

In some embodiments, Z is O.

In some embodiments, the compound of formula (II) is represented by the following formula:

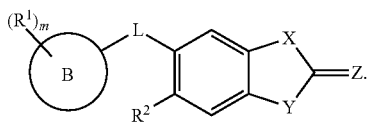

In one aspect, the invention features a compound of formula (III):

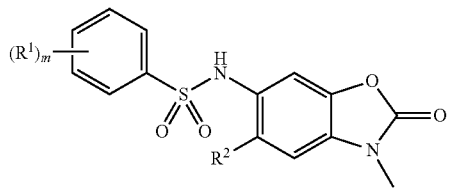

formula (III)

wherein:
m is an integer from 0 to 5;
each $R^1$ is independently selected from $C_1$-$C_6$ alkyl, $C_1$-$C_6$ alkoxy, $C_1$-$C_6$ haloalkyl, $C_{1-6}$ haloalkoxy, halo, acetyl, —$NO_2$, aryl, aralkyl, heteroaryl, —$SO_2$-aryl, —C(O)—$NR^b$-aryl, —C(O)-aralkyl, —C(O)—$C_{1-6}$ alkoxy, —$NR^b$—$SO_2$-aryl, wherein each aryl, aralkyl and heteroaryl group is optionally substituted with 0-3 occurrences of $R^c$ and wherein two $R^1$ groups taken together with the carbon atoms to which they are attached form a heterocyclyl ring;
each $R^2$ is independently selected from $C_1$-$C_6$ alkyl and halo;
each $R^b$ is independently selected from hydrogen, $C_{1-6}$ aralkyl, and $C_1$-$C_6$ alkyl substituted with 0-1 occurrences of $R^c$;
$R^c$ is independently selected from $C_{1-6}$ alkyl, $C_{1-6}$ alkoxy, $C_{1-6}$ haloalkyl, halo, $NR^dR^d$, and heterocyclyl and wherein two $R^c$ groups taken together with the carbon atoms to which they are attached form a heterocyclyl ring; and
$R^d$ is independently selected from H and $C_{1-6}$ alkyl.

In some embodiments, each $R^1$ is independently selected from $C_1$-$C_6$ alkyl, $C_1$-$C_6$ alkoxy, $C_1$-$C_6$ haloalkyl, halo, acetyl and —$NO_2$.

In some embodiments, each $R^2$ is independently $C_1$-$C_6$ alkyl.

In some embodiments, m is 0. In some embodiments, m is 1. In some embodiments, $R^1$ is halo (e.g., fluoro, chloro or bromo). In some embodiments, $R^1$ is $C_1$-$C_6$ alkyl (e.g., methyl). In some embodiments, $R^1$ is $C_1$-$C_6$ alkoxy (e.g., methoxy). In some embodiments, $R^1$ is acetyl. In some embodiments, $R^1$ is —$NO_2$.

In some embodiments, m is 2. In some embodiments, one $R^1$ is halo (e.g., fluoro or chloro) and the other is $C_1$-$C_6$ alkoxy (e.g., methoxy). In some embodiments, both $R^1$ are halo (e.g., fluoro or chloro). In some embodiments, one $R^1$ is $C_1$-$C_6$ alkyl (e.g., methyl) and the other is $C_1$-$C_6$ alkoxy (e.g., methoxy). In some embodiments, both $R^1$ are $C_1$-$C_6$ alkoxy (e.g., methoxy). In some embodiments, both $R^1$ are $C_{1-6}$ alkyl (e.g., methyl).

In some embodiments, $R^2$ is methyl.

In one aspect, the invention features a pharmaceutical composition comprising a compound of formula (IV):

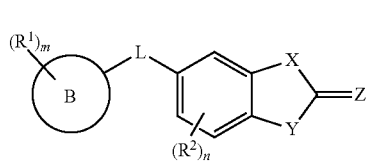

formula (IV)

wherein:
m is an integer from 0 to 5;
each $R^1$ is independently selected from $C_1$-$C_6$ alkyl, $C_1$-$C_6$ alkoxy, $C_1$-$C_6$ haloalkyl, $C_{1-6}$ haloalkoxy, halo, acetyl, —$NO_2$, aryl, aralkyl, heteroaryl, —$SO_2$-aryl, —C(O)—$NR^b$-aryl, —C(O)-aralkyl, —C(O)—$C_{1-6}$ alkoxy, —$NR^b$—$SO_2$-aryl, wherein each aryl, aralkyl and heteroaryl group is optionally substituted with 0-3 occurrences of $R^c$ and wherein two $R^1$ groups taken together with the carbon atoms to which they are attached form a heterocyclyl ring;
n is an integer from 0 to 3;
each $R^2$ is independently selected from $C_1$-$C_6$ alkyl and halo;
B is aryl, monocyclic heteroaryl, cycloalkyl, heterocyclyl, $C_{1-6}$ aralkyl, or $C_{1-6}$ heteroaralkyl;
L is a linker selected from —$SO_2$—, —$SO_2NR^a$— and —$NR^aSO_2$—;
each $R^a$ is independently selected from hydrogen and $C_1$-$C_6$ alkyl;
X and Y are each independently selected from O, S, $NR^b$ and $CH_2$;
Z is O or S;
each $R^b$ is independently selected from hydrogen, $C_{1-6}$ aralkyl, and $C_1$-$C_6$ alkyl substituted with 0-1 occurrences of $R^c$; and
$R^c$ is independently selected from $C_{1-6}$ alkyl, $C_{1-6}$ alkoxy, $C_{1-6}$ haloalkyl, halo, $NR^dR^d$, and heterocyclyl and wherein two $R^c$ groups taken together with the carbon atoms to which they are attached form a heterocyclyl ring; and
$R^d$ is independently selected from H and $C_{1-6}$ alkyl.

In some embodiments, B is monocyclic aryl (e.g., phenyl). In some embodiments, B is unsubstituted phenyl. In some embodiments, B is phenyl substituted with 1 $R^1$. In some embodiments, $R^1$ is halo (e.g., fluoro, chloro or bromo). In some embodiments, $R^1$ is $C_1$-$C_6$ alkyl (e.g., methyl or ethyl). In some embodiments, $R^1$ is $C_1$-$C_6$ alkoxy (e.g., methoxy). In some embodiments, $R^1$ is haloalkyl (e.g., trifluoromethyl). In some embodiments, $R^1$ is acetyl. In some embodiments, $R^1$ is —$NR^b$-acetyl (e.g., acetamide). In some embodiments, $R^1$ is —$NO_2$. In some embodiments, $R^1$ is —$NR^b$—$SO_2$-aryl (e.g., —NR$^b$—SO$_2$-phenyl). In some embodiments, R$^b$ is H. In some embodiments, R$^1$ is —NH—SO$_2$-phenyl substituted with two occurrences of R$^c$. In some embodiments, one R$^c$ is C$_{1-6}$ alkoxy (e.g., methoxy) and one R$^c$ is halo (e.g., fluoro or chloro). In some embodiments, both R$^c$ are halo (e.g., fluoro or chloro). In some embodiments, one R$^c$ is C$_{1-6}$ alkoxy (e.g., methoxy) and one R$^c$ is C$_{1-6}$ alkyl (e.g., methyl).

In some embodiments, B is phenyl substituted with two R$^1$. In some embodiments, one R$^1$ is halo (e.g., fluoro or chloro) and the other is C$_1$-C$_6$ alkoxy (e.g., methoxy). In some embodiments, both R$^1$ are halo (e.g., fluoro or chloro). In some embodiments, one R$^1$ is halo (e.g., fluoro or chloro) and one R$^1$ is haloalkyl (e.g., trifluoromethyl). In some embodiments, one R$^1$ is halo (e.g., fluoro or chloro) and one R$^1$ is C$_{1-6}$ alkyl (e.g., methyl or ethyl). In some embodiments, one R$^1$ is C$_1$-C$_6$ alkyl (e.g., methyl) and the other is C$_1$-C$_6$ alkoxy (e.g., methoxy). In some embodiments, both R$^1$ are C$_1$-C$_6$ alkyl (e.g., methyl). In some embodiments, both R$^1$ are C$_1$-C$_6$ alkoxy (e.g., methoxy). In some embodiments, two R$^1$ groups taken together with the carbon atoms to which they are attached form a heterocyclyl ring. In some embodiments, two R$^1$ groups taken together with the carbon atoms to which they are attached form the following compound:

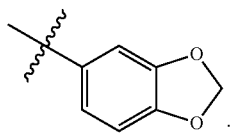

In some embodiments, two R$^1$ groups taken together with the carbon atoms to which they are attached form the following compound:

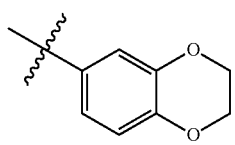 [SMILES: *c1ccc2c(c1)OCCO2]

In some embodiments, B is bicyclic aryl (e.g., naphthyl). In some embodiments, B is unsubstituted naphthyl.

In some embodiments, B is monocyclic heteroaryl, e.g., a 5-membered monocyclic heteroaryl (e.g., thiophenyl). In some embodiments, B is a 6-membered monocyclic heteroaryl, e.g., a 6-membered nitrogen-containing monocyclic heteroaryl (e.g., pyridyl). In some embodiments, B is unsubstituted pyridyl. In some embodiments, B is pyridyl substituted with two R$^1$. In some embodiments, one R$^1$ is halo (e.g., chloro) and the other is haloalkyl (e.g., trifluoromethyl).

In some embodiments, B is bicyclic heteroaryl, e.g., a 10-membered bicyclic heteroaryl (e.g., a 10-membered nitrogen containing bicyclic heteroaryl). In some embodiments, B is a 10-membered nitrogen containing bicyclic heteroaryl (e.g., quinolyl). In some embodiments, B is unsubstituted quinolyl.

In some embodiments, B is a monocyclic heterocyclyl (e.g., a 6-membered monocyclic heterocyclyl). In some embodiments, B is a 6-membered nitrogen containing monocyclic heterocyclyl (e.g., piperazinyl). In some embodiments, B is unsubstituted piperazinyl. In some embodiments, B is piperazinyl substituted with an R$^1$. In some embodiments, R$^1$ is —SO$_2$-aryl (e.g., phenyl or naphthyl). In some embodiments, R$^1$ is —SO$_2$-phenyl substituted with 0 occurrences of R$^c$. In some embodiments, R$^1$ is —SO$_2$-naphthyl. In some embodiments, R$^1$ is —SO$_2$-phenyl substituted with 1 occurrence of R$^c$. In some embodiments, R$^c$ is C$_{1-6}$ alkoxy (e.g., methoxy). In some embodiments, R$^c$ is halo (e.g., fluoro or chloro).

In some embodiments, R$^1$ is —SO$_2$-phenyl substituted with 2 occurrences of R$^c$. In some embodiments, one R$^c$ is C$_{1-6}$ alkoxy (e.g., methoxy) and the other R$^c$ is halo (e.g., chloro or fluoro). In some embodiments, both R$^c$ are halo (e.g., fluoro or chloro). In some embodiments, both R$^c$ taken together form a heterocyclyl. In some embodiments, both R$^c$ are taken together to form the compound represented below:

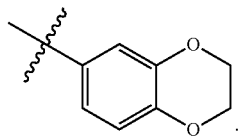 [SMILES: *c1ccc2c(c1)OCCO2 ; "."]

In some embodiments, R$^1$ is aralkyl (e.g., benzyl).

In some embodiments, R$^1$ is —C(O)—C$_{1-6}$ alkoxy (e.g., —C(O)-t-butoxy).

In some embodiments, R$^1$ is —SO$_2$-heteroaryl (e.g., —SO$_2$-pyridyl). In some embodiments, R$^1$ is —SO$_2$-pyridyl substituted with 0 occurrences of R$^c$. In some embodiments, R$^1$ is —SO$_2$-pyridyl substituted with 1 occurrence of R$^c$. In some embodiments, R$^c$ is haloalkyl (e.g., trifluoromethyl).

In some embodiments, R$^1$ is —C(O)-aralkyl (e.g., —C(O)-benzyl). In some embodiments, R$^1$ is —C(O)-benzyl substituted with 0 occurrences of R$^c$. In some embodiments, R$^1$ is —C(O)-benzyl substituted with 1 occurrence of R$^c$. In some embodiments, R$^c$ is haloalkyl (e.g., trifluoromethyl).

In some embodiments, B is a monocyclic heterocyclyl (e.g., a 7-membered monocyclic heterocyclyl). In some embodiments, B is a 7-membered nitrogen containing monocyclic heterocyclyl (e.g., 1,4-diazepanyl). In some embodiments, B is unsubstituted 1,4-diazepanyl. In some embodiments, B is 1,4-diazepanyl substituted with an R$^1$. In some embodiments, R$^1$ is —SO$_2$-aryl (e.g., phenyl or naphthyl). In some embodiments, R$^1$ is —SO$_2$-phenyl substituted with 0 occurrences of R$^c$. In some embodiments, R$^1$ is —SO$_2$-naphthyl. In some embodiments, R$^1$ is —SO$_2$-phenyl substituted with 1 occurrence of R$^c$. In some embodiments, R$^c$ is C$_{1-6}$ alkoxy (e.g., methoxy). In some embodiments, R$^c$ is halo (e.g., fluoro or chloro).

In some embodiments, R$^1$ is phenyl substituted with 2 occurrences of R$^c$. In some embodiments, one R$^c$ is C$_{1-6}$ alkoxy (e.g., methoxy) and the other R$^c$ is halo (e.g., chloro or fluoro). In some embodiments, both R$^c$ are halo (e.g., fluoro or chloro). In some embodiments, both R$^c$ taken together form a heterocyclyl. In some embodiments, both R$^c$ are taken together to form the compound represented below:

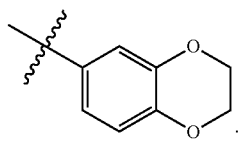 [SMILES: *c1ccc2c(c1)OCCO2 ; "."]

In some embodiments, R$^1$ is aralkyl (e.g., benzyl).

In some embodiments, R$^1$ is —C(O)—C$_{1-6}$ alkoxy (e.g., —C(O)-t-butoxy).

In some embodiments, $R^1$ is —$SO_2$-heteroaryl (e.g., —$SO_2$-pyridyl). In some embodiments, $R^1$ is —$SO_2$-pyridyl substituted with 0 occurrences of $R^c$. In some embodiments, $R^1$ is —$SO_2$-pyridyl substituted with 1 occurrence of $R^c$. In some embodiments, $R^c$ is haloalkyl (e.g., trifluoromethyl).

In some embodiments, In some embodiments, B is a monocyclic heterocyclyl (e.g., a 6-membered monocyclic heterocyclyl). In some embodiments, B is a 6-membered nitrogen containing monocyclic heterocyclyl (e.g., piperidinyl). In some embodiments, B is unsubstituted piperidinyl. In some embodiments, B is piperidinyl substituted with an $R^1$. In some embodiments, $R^1$ is —C(O)—$NR^b$-aryl (e.g., —C(O)—$NR^b$-phenyl. In some embodiments, $R^b$ is H. In some embodiments, $R^1$ is —C(O)—NH-phenyl substituted with two occurrences of $R^c$. In some embodiments, both $R^c$ are $C_{1-6}$ alkyl (e.g., methyl).

In some embodiments, B is cycloalkyl (e.g., cyclohexyl).

In some embodiments, B is $C_{1-6}$ aralkyl (e.g., benzyl). In some embodiments, B is benzyl substituted with 0 occurrences of $R^1$.

In some embodiments, n is 0. In some embodiments, n is 1. In some embodiments, $R^2$ is $C_1$-$C_6$ alkyl (e.g., methyl). In some embodiments, $R^2$ is halo (e.g., fluoro, chloro or bromo).

In some embodiments, L is —$SO_2NR^a$—. In some embodiments, $R^a$ is hydrogen. In some embodiments, $R^a$ is $C_1$-$C_6$ alkyl (e.g., methyl, ethyl or isopropyl). In some embodiments, L is —$NR^aSO_2$—. In some embodiments, $R^a$ is hydrogen. In some embodiments, $R^a$ is $C_1$-$C_6$ alkyl (e.g., methyl, ethyl or isopropyl).

In some embodiments, X is S. In some embodiments, X is O. In some embodiments, X is $NR^b$. In some embodiments, $R^b$ is hydrogen. In some embodiments, $R^b$ is $C_1$-$C_6$ alkyl substituted with 0 occurrences of $R^c$ (e.g., methyl, ethyl, isopropyl or sec-butyl). In some embodiments, $R^b$ is aralkyl (e.g., benzyl or phenethyl). In some embodiments, $R^b$ is $C_{1-6}$ alkyl substituted with 1 occurrence of $R^c$ (e.g., methyl, ethyl or propyl). In some embodiments, $R^c$ is $C_{1-6}$ alkoxy (e.g., methoxy). In some embodiments, $R^c$ is heterocyclyl (e.g., morpholinyl or piperidinyl). In some embodiments, $R^c$ is $NR^dR^d$. In some embodiments, $R^d$ is selected from $C_{1-6}$ alkyl (e.g., methyl).

In some embodiments, Y is S. In some embodiments, Y is O. In some embodiments, Y is $NR^b$. In some embodiments, $R^b$ is hydrogen. In some embodiments, $R^b$ is $C_1$-$C_6$ alkyl substituted with 0 occurrences of $R^c$ (e.g., methyl, ethyl, isopropyl or sec-butyl). In some embodiments, $R^b$ is aralkyl (e.g., benzyl or phenethyl). In some embodiments, $R^b$ is $C_{1-6}$ alkyl substituted with 1 occurrence of $R^c$ (e.g., methyl, ethyl or propyl). In some embodiments, $R^c$ is $C_{1-6}$ alkoxy (e.g., methoxy). In some embodiments, $R^c$ is heterocyclyl (e.g., morpholinyl or piperidinyl). In some embodiments, $R^c$ is $NR^dR^d$. In some embodiments, $R^d$ is selected from $C_{1-6}$ alkyl (e.g., methyl).

In some embodiments, X and Y are both S. In some embodiments, X and Y are both $NR^b$. In some embodiments, X and Y are both $NCH_3$. In some embodiments, one of X and Y is O and the other is S. In some embodiments, one of X and Y is O and the other is $NR^b$. In some embodiments, $R^b$ is hydrogen. In some embodiments, $R^b$ is $C_1$-$C_6$ alkyl (e.g., methyl, ethyl, isopropyl or sec-butyl).

In some embodiments, one of X and Y is S and the other is $NR^b$. In some embodiments, $R^b$ is hydrogen. In some embodiments, $R^b$ is $C_1$-$C_6$ alkyl (e.g., methyl, ethyl, isopropyl or sec-butyl).

In some embodiments, Z is O.

In one aspect, the invention features a method of treating cancer comprising administering to a subject a compound of formula (IV):

formula (IV)

wherein:

m is an integer from 0 to 5;

each $R^1$ is independently selected from $C_1$-$C_6$ alkyl, $C_1$-$C_6$ alkoxy, $C_1$-$C_6$ haloalkyl, $C_{1-6}$ haloalkoxy, halo, acetyl, —$NO_2$, aryl, aralkyl, heteroaryl, —$SO_2$-aryl, —C(O)—$NR^b$-aryl, —C(O)-aralkyl, —C(O)—$C_{1-6}$ alkoxy, —$NR^b$—$SO_2$-aryl, wherein each aryl, aralkyl and heteroaryl group is optionally substituted with 0-3 occurrences of $R^c$ and wherein two $R^1$ groups taken together with the carbon atoms to which they are attached form a heterocyclyl ring;

n is an integer from 0 to 3;

each $R^2$ is independently selected from $C_1$-$C_6$ alkyl and halo;

B is aryl, monocyclic heteroaryl, cycloalkyl, heterocyclyl, $C_{1-6}$ aralkyl, or $C_{1-6}$ heteroaralkyl;

L is a linker selected from —$SO_2$—, —$SO_2NR^a$— and —$NR^aSO_2$—;

each $R^a$ is independently selected from hydrogen and $C_1$-$C_6$ alkyl;

X and Y are each independently selected from O, S, $NR^b$ and $CH_2$;

Z is O or S;

each $R^b$ is independently selected from hydrogen, $C_{1-6}$ aralkyl, and $C_1$-$C_6$ alkyl substituted with 0-1 occurrences of $R^c$; and $R^c$ is independently selected from $C_{1-6}$ alkyl, $C_{1-6}$ alkoxy, $C_{1-6}$ haloalkyl, halo, $NR^dR^d$, and heterocyclyl and wherein two $R^c$ groups taken together with the carbon atoms to which they are attached form a heterocyclyl ring; and $R^d$ is independently selected from H and $C_{1-6}$ alkyl.

In some embodiments, B is monocyclic aryl (e.g., phenyl). In some embodiments, B is unsubstituted phenyl. In some embodiments, B is phenyl substituted with 1 $R^1$. In some embodiments, $R^1$ is halo (e.g., fluoro, chloro or bromo). In some embodiments, $R^1$ is $C_1$-$C_6$ alkyl (e.g., methyl or ethyl). In some embodiments, $R^1$ is $C_1$-$C_6$ alkoxy (e.g., methoxy). In some embodiments, $R^1$ is haloalkyl (e.g., trifluoromethyl). In some embodiments, $R^1$ is acetyl. In some embodiments, $R^1$ is —$NR^b$-acetyl (e.g., acetamide). In some embodiments, $R^1$ is —$NO_2$. In some embodiments, $R^1$ is —$NR^b$—$SO_2$-aryl (e.g., —$NR^b$—$SO_2$-phenyl). In some embodiments, $R^b$ is H. In some embodiments, $R^1$ is —NH—$SO_2$-phenyl substituted with two occurrences of $R^c$. In some embodiments, one $R^c$ is $C_{1-6}$ alkoxy (e.g., methoxy) and one $R^c$ is halo (e.g., fluoro or chloro). In some embodiments, both $R^c$ are halo (e.g., fluoro or chloro). In some embodiments, one $R^c$ is $C_{1-6}$ alkoxy (e.g., methoxy) and one $R^c$ is $C_{1-6}$ alkyl (e.g., methyl).

In some embodiments, B is phenyl substituted with two $R^1$. In some embodiments, one $R^1$ is halo (e.g., fluoro or chloro) and the other is $C_1$-$C_6$ alkoxy (e.g., methoxy). In some embodiments, both $R^1$ are halo (e.g., fluoro or chloro). In some embodiments, one $R^1$ is halo (e.g., fluoro or chloro) and one $R^1$ is haloalkyl (e.g., trifluoromethyl). In some embodiments, one $R^1$ is halo (e.g., fluoro or chloro) and one $R^1$ is $C_{1-6}$ alkyl (e.g., methyl or ethyl). In some embodiments, one $R^1$ is $C_1$-$C_6$ alkyl (e.g., methyl) and the other is $C_1$-$C_6$ alkoxy (e.g., methoxy). In some embodiments, both $R^1$ are $C_1$-$C_6$ alkyl (e.g., methyl). In some embodiments, both $R^1$ are $C_1$-$C_6$ alkoxy (e.g., methoxy). In some embodiments, two $R^1$ groups taken together with the carbon atoms to which they are attached form a heterocyclyl ring. In some embodiments, two $R^1$ groups taken together with the carbon atoms to which they are attached form the following compound:

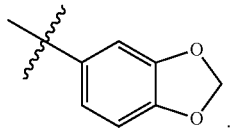 [SMILES: *c1ccc2c(c1)OCO2 ; "."]

In some embodiments, two $R^1$ groups taken together with the carbon atoms to which they are attached form the following compound:

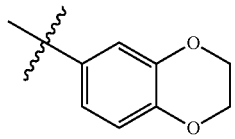 [SMILES: *c1ccc2c(c1)OCCO2]

In some embodiments, B is bicyclic aryl (e.g., naphthyl). In some embodiments, B is unsubstituted naphthyl.

In some embodiments, B is monocyclic heteroaryl, e.g., a 5-membered monocyclic heteroaryl (e.g., thiophenyl). In some embodiments, B is a 6-membered monocyclic heteroaryl, e.g., a 6-membered nitrogen-containing monocyclic heteroaryl (e.g., pyridyl). In some embodiments, B is unsubstituted pyridyl. In some embodiments, B is pyridyl substituted with two $R^1$. In some embodiments, one $R^1$ is halo (e.g., chloro) and the other is haloalkyl (e.g., trifluoromethyl).

In some embodiments, B is bicyclic heteroaryl, e.g., a 10-membered bicyclic heteroaryl (e.g., a 10-membered nitrogen containing bicyclic heteroaryl). In some embodiments, B is a 10-membered nitrogen containing bicyclic heteroaryl (e.g., quinolyl). In some embodiments, B is unsubstituted quinolyl.

In some embodiments, B is a monocyclic heterocyclyl (e.g., a 6-membered monocyclic heterocyclyl). In some embodiments, B is a 6-membered nitrogen containing monocyclic heterocyclyl (e.g., piperazinyl). In some embodiments, B is unsubstituted piperazinyl. In some embodiments, B is piperazinyl substituted with an $R^1$. In some embodiments, $R^1$ is —$SO_2$-aryl (e.g., phenyl or naphthyl). In some embodiments, $R^1$ is —$SO_2$-phenyl substituted with 0 occurrences of $R^c$. In some embodiments, $R^1$ is —$SO_2$-naphthyl. In some embodiments, $R^1$ is —$SO_2$-phenyl substituted with 1 occurrence of $R^c$. In some embodiments, $R^c$ is $C_{1-6}$ alkoxy (e.g., methoxy). In some embodiments, $R^c$ is halo (e.g., fluoro or chloro).

In some embodiments, $R^1$ is —$SO_2$-phenyl substituted with 2 occurrences of $R^c$. In some embodiments, one $R^c$ is $C_{1-6}$ alkoxy (e.g., methoxy) and the other $R^c$ is halo (e.g., chloro or fluoro). In some embodiments, both $R^c$ are halo (e.g., fluoro or chloro). In some embodiments, both $R^c$ taken together form a heterocyclyl. In some embodiments, both $R^c$ are taken together to form the compound represented below:

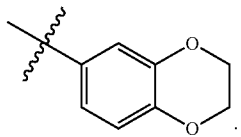 [SMILES: *c1ccc2c(c1)OCCO2 ; "."]

In some embodiments, $R^1$ is aralkyl (e.g., benzyl).
In some embodiments, $R^1$ is —C(O)—$C_{1-6}$ alkoxy (e.g., —C(O)-t-butoxy).
In some embodiments, $R^1$ is —$SO_2$-heteroaryl (e.g., —$SO_2$-pyridyl). In some embodiments, $R^1$ is —$SO_2$-pyridyl substituted with 0 occurrences of $R^c$. In some embodiments, $R^1$ is —$SO_2$-pyridyl substituted with 1 occurrence of $R^c$. In some embodiments, $R^c$ is haloalkyl (e.g., trifluoromethyl).
In some embodiments, $R^1$ is —C(O)-aralkyl (e.g., —C(O)-benzyl). In some embodiments, $R^1$ is —C(O)-benzyl substituted with 0 occurrences of $R^c$. In some embodiments, $R^1$ is —C(O)-benzyl substituted with 1 occurrence of $R^c$. In some embodiments, $R^c$ is haloalkyl (e.g., trifluoromethyl).

In some embodiments, B is a monocyclic heterocyclyl (e.g., a 7-membered monocyclic heterocyclyl). In some embodiments, B is a 7-membered nitrogen containing monocyclic heterocyclyl (e.g., 1,4-diazepanyl). In some embodiments, B is unsubstituted 1,4-diazepanyl. In some embodiments, B is 1,4-diazepanyl substituted with an $R^1$. In some embodiments, $R^1$ is —$SO_2$-aryl (e.g., phenyl or naphthyl). In some embodiments, $R^1$ is —$SO_2$-phenyl substituted with 0 occurrences of $R^c$. In some embodiments, $R^1$ is —$SO_2$-naphthyl. In some embodiments, $R^1$ is —$SO_2$-phenyl substituted with 1 occurrence of $R^c$. In some embodiments, $R^c$ is $C_{1-6}$ alkoxy (e.g., methoxy). In some embodiments, $R^c$ is halo (e.g., fluoro or chloro).

In some embodiments, $R^1$ is phenyl substituted with 2 occurrences of $R^c$. In some embodiments, one $R^c$ is $C_{1-6}$ alkoxy (e.g., methoxy) and the other $R^c$ is halo (e.g., chloro or fluoro). In some embodiments, both $R^c$ are halo (e.g., fluoro or chloro). In some embodiments, both $R^c$ taken together form a heterocyclyl. In some embodiments, both $R^c$ are taken together to form the compound represented below:

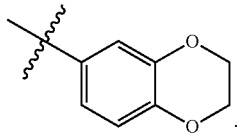 [SMILES: *c1ccc2c(c1)OCCO2 ; "."]

In some embodiments, $R^1$ is aralkyl (e.g., benzyl).
In some embodiments, $R^1$ is —C(O)—$C_{1-6}$ alkoxy (e.g., —C(O)-t-butoxy).
In some embodiments, $R^1$ is —$SO_2$-heteroaryl (e.g., —$SO_2$-pyridyl). In some embodiments, $R^1$ is —$SO_2$-pyridyl substituted with 0 occurrences of $R^c$. In some embodiments, $R^1$ is —$SO_2$-pyridyl substituted with 1 occurrence of $R^c$. In some embodiments, $R^c$ is haloalkyl (e.g., trifluoromethyl).
In some embodiments, In some embodiments, B is a monocyclic heterocyclyl (e.g., a 6-membered monocyclic heterocyclyl). In some embodiments, B is a 6-membered nitrogen containing monocyclic heterocyclyl (e.g., piperidinyl). In some embodiments, B is unsubstituted piperidinyl. In some embodiments, B is piperidinyl substituted with an $R^1$. In some embodiments, $R^1$ is —C(O)—$NR^b$-aryl (e.g., —C(O)—$NR^b$-phenyl. In some embodiments, $R^b$ is H. In some embodiments, $R^1$ is —C(O)—NH-phenyl substituted with two occurrences of $R^c$. In some embodiments, both $R^c$ are $C_{1-6}$ alkyl (e.g., methyl).

In some embodiments, B is cycloalkyl (e.g., cyclohexyl).

In some embodiments, B is $C_{1-6}$ aralkyl (e.g., benzyl). In some embodiments, B is benzyl substituted with 0 occurrences of $R^1$.

In some embodiments, n is 0. In some embodiments, n is 1. In some embodiments, $R^2$ is $C_1$-$C_6$ alkyl (e.g., methyl). In some embodiments, $R^2$ is halo (e.g., fluoro, chloro or bromo).

In some embodiments, L is —$SO_2NR^a$—. In some embodiments, $R^a$ is hydrogen. In some embodiments, $R^a$ is $C_1$-$C_6$ alkyl (e.g., methyl, ethyl or isopropyl). In some embodiments, L is —$NR^aSO_2$—. In some embodiments, $R^a$ is hydrogen. In some embodiments, $R^a$ is $C_1$-$C_6$ alkyl (e.g., methyl, ethyl or isopropyl).

In some embodiments, X is S. In some embodiments, X is O. In some embodiments, X is $NR^b$. In some embodiments, $R^b$ is hydrogen. In some embodiments, $R^b$ is $C_1$-$C_6$ alkyl substituted with 0 occurrences of $R^c$ (e.g., methyl, ethyl, isopropyl or sec-butyl). In some embodiments, $R^b$ is aralkyl (e.g., benzyl or phenethyl). In some embodiments, $R^b$ is $C_{1-6}$ alkyl substituted with 1 occurrence of $R^c$ (e.g., methyl, ethyl or propyl). In some embodiments, $R^c$ is $C_{1-6}$ alkoxy (e.g., methoxy). In some embodiments, $R^c$ is heterocyclyl (e.g., morpholinyl or piperidinyl). In some embodiments, $R^c$ is $NR^dR^d$. In some embodiments, $R^d$ is selected from $C_{1-6}$ alkyl (e.g., methyl).

In some embodiments, Y is S. In some embodiments, Y is O. In some embodiments, Y is $NR^b$. In some embodiments, $R^b$ is hydrogen. In some embodiments, $R^b$ is $C_1$-$C_6$ alkyl substituted with 0 occurrences of $R^c$ (e.g., methyl, ethyl, isopropyl or sec-butyl). In some embodiments, $R^b$ is aralkyl (e.g., benzyl or phenethyl). In some embodiments, $R^b$ is $C_{1-6}$ alkyl substituted with 1 occurrence of $R^c$ (e.g., methyl, ethyl or propyl). In some embodiments, $R^c$ is $C_{1-6}$ alkoxy (e.g., methoxy). In some embodiments, $R^c$ is heterocyclyl (e.g., morpholinyl or piperidinyl). In some embodiments, $R^c$ is $NR^dR^d$. In some embodiments, $R^d$ is selected from $C_{1-6}$ alkyl (e.g., methyl).

In some embodiments, X and Y are both S. In some embodiments, X and Y are both $NR^b$. In some embodiments, X and Y are both $NCH_3$. In some embodiments, one of X and Y is O and the other is S. In some embodiments, one of X and Y is O and the other is $NR^b$. In some embodiments, $R^b$ is hydrogen. In some embodiments, $R^b$ is $C_1$-$C_6$ alkyl (e.g., methyl, ethyl, isopropyl or sec-butyl).

In some embodiments, one of X and Y is S and the other is $NR^b$. In some embodiments, $R^b$ is hydrogen. In some embodiments, $R^b$ is $C_1$-$C_6$ alkyl (e.g., methyl, ethyl, isopropyl or sec-butyl).

In some embodiments, Z is O.

In one aspect, the invention features a method of modulating (e.g., increasing or decreasing) the level of PKM2 activity and/or glycolysis (e.g., modulating the endogenous ability of a cell in the patient to down regulate PKM2) in a patient in need thereof. The method comprises the step of administering an effective amount of a compound described herein to the patient in need thereof, thereby modulating (e.g., increasing or decreasing) the level of PKM2 activity and/or glycolysis in the patient. In some embodiments of the invention an activator is used to maintain PKM2 in its active conformation or activate pyruvate kinase activity in proliferating cells as a means to divert glucose metabolites into catabolic rather than anabolic processes in the patient.

In another aspect, the invention features a method of regulating cell proliferation in a patient in need thereof. The method comprises the step of administering an effective amount of a compound described herein to the patient in need thereof, thereby regulating cell proliferation in the patient. E.g., this method can modulate growth of a transformed cell, e.g., a cancer cell, or generally modulate growth in a PKM2-dependent cell that undergoes aerobic glycolysis.

In another aspect, the invention features a method of treating a patient suffering from or susceptible to a disease or disorder associated with the function of PKM2 in a patient in need thereof. The method comprises the step of administering an effective amount of a compound described herein to the patient in need thereof, thereby treating, preventing or ameliorating the disease or disorder in the patient. In another embodiment the modulator is provided in a pharmaceutical composition.

In another embodiment the method includes identifying or selecting a patient who would benefit from modulation (e.g., activation or inhibition) of PKM2. E.g., the patient can be identified on the basis of the level of PKM2 activity in a cell of the patient (e.g., as opposed to merely being in need of treatment of the disorder itself, e.g., cancer). In another embodiment the selected patient is a patient suffering from or susceptible to a disorder or disease identified herein, e.g., a disorder characterized by unwanted cell growth or proliferation, e.g., cancer, obesity, diabetes, atherosclerosis, restenosis, and autoimmune diseases.

In another embodiment the compound described herein is administered at a dosage and frequency sufficient to increase lactate production or oxidative phosphorylation.

The term "halo" or "halogen" refers to any radical of fluorine, chlorine, bromine or iodine.

The term "alkyl" refers to a hydrocarbon chain that may be a straight chain or branched chain, containing the indicated number of carbon atoms. For example, $C_1$-$C_{12}$ alkyl indicates that the group may have from 1 to 12 (inclusive) carbon atoms in it. The term "haloalkyl" refers to an alkyl in which one or more hydrogen atoms are replaced by halo, and includes alkyl moieties in which all hydrogens have been replaced by halo (e.g., perfluoroalkyl). The terms "arylalkyl" or "aralkyl" refer to an alkyl moiety in which an alkyl hydrogen atom is replaced by an aryl group. Aralkyl includes groups in which more than one hydrogen atom has been replaced by an aryl group. Examples of "arylalkyl" or "aralkyl" include benzyl, 2-phenylethyl, 3-phenylpropyl, 9-fluorenyl, benzhydryl, and trityl groups.

The term "alkylene" refers to a divalent alkyl, e.g., —$CH_2$—, —$CH_2CH_2$—, and —$CH_2CH_2CH_2$—.

The term "alkenyl" refers to a straight or branched hydrocarbon chain containing 2-12 carbon atoms and having one or more double bonds. Examples of alkenyl groups include, but are not limited to, allyl, propenyl, 2-butenyl, 3-hexenyl and 3-octenyl groups. One of the double bond carbons may optionally be the point of attachment of the alkenyl substituent. The term "alkynyl" refers to a straight or branched hydrocarbon chain containing 2-12 carbon atoms and characterized in having one or more triple bonds. Examples of alkynyl groups include, but are not limited to, ethynyl, propargyl, and 3-hexynyl. One of the triple bond carbons may optionally be the point of attachment of the alkynyl substituent.

The terms "alkylamino" and "dialkylamino" refer to —NH (alkyl) and —$NH(alkyl)_2$ radicals respectively. The term "aralkylamino" refers to a —NH(aralkyl) radical. The term alkylaminoalkyl refers to a (alkyl)NH-alkyl-radical; the term dialkylaminoalkyl refers to a $(alkyl)_2$N-alkyl-radical The term "alkoxy" refers to an —O-alkyl radical. The term "mercapto" refers to an SH radical. The term "thioalkoxy" refers to an —S-alkyl radical. The term thioaryloxy refers to an —S-aryl radical.

The terms "arylalkyl" or "aralkyl" refer to an alkyl moiety in which an alkyl hydrogen atom is replaced by an aryl group. Aralkyl includes groups in which more than one hydrogen atom has been replaced by an aryl group. Examples of "arylalkyl" or "aralkyl" include benzyl, 2-phenylethyl, 3-phenylpropyl, 9-fluorenyl, benzhydryl, and trityl groups.

The term "aryl" refers to an aromatic monocyclic, bicyclic, or tricyclic hydrocarbon ring system, wherein any ring atom capable of substitution can be substituted (e.g., by one or more substituents). Examples of aryl moieties include, but are not limited to, phenyl, naphthyl, and anthracenyl.

The term "cycloalkyl" as employed herein includes saturated cyclic, bicyclic, tricyclic, or polycyclic hydrocarbon groups having 3 to 12 carbons. Any ring atom can be substituted (e.g., by one or more substituents). The cycloalkyl groups can contain fused rings. Fused rings are rings that share a common carbon atom. Examples of cycloalkyl moieties include, but are not limited to, cyclopropyl, cyclohexyl, methylcyclohexyl, adamantyl, and norbornyl.

The term "heterocyclyl" refers to a nonaromatic 3-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). The heteroatom may optionally be the point of attachment of the heterocyclyl substituent. Any ring atom can be substituted (e.g., by one or more substituents). The heterocyclyl groups can contain fused rings. Fused rings are rings that share a common carbon atom. Examples of heterocyclyl include, but are not limited to, tetrahydrofuranyl, tetrahydropyranyl, piperidinyl, morpholino, pyrrolinyl, pyrimidinyl, quinolinyl, and pyrrolidinyl.

The term "cycloalkenyl" refers to partially unsaturated, nonaromatic, cyclic, bicyclic, tricyclic, or polycyclic hydrocarbon groups having 5 to 12 carbons, preferably 5 to 8 carbons. The unsaturated carbon may optionally be the point of attachment of the cycloalkenyl substituent. Any ring atom can be substituted (e.g., by one or more substituents). The cycloalkenyl groups can contain fused rings. Fused rings are rings that share a common carbon atom. Examples of cycloalkenyl moieties include, but are not limited to, cyclohexenyl, cyclohexadienyl, or norbornenyl.

The term "heterocycloalkenyl" refers to a partially saturated, nonaromatic 5-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). The unsaturated carbon or the heteroatom may optionally be the point of attachment of the heterocycloalkenyl substituent. Any ring atom can be substituted (e.g., by one or more substituents). The heterocycloalkenyl groups can contain fused rings. Fused rings are rings that share a common carbon atom. Examples of heterocycloalkenyl include but are not limited to tetrahydropyridyl and dihydropyranyl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). Any ring atom can be substituted (e.g., by one or more substituents).

The terms "hetaralkyl" and "heteroaralkyl", as used herein, refers to an alkyl group substituted with a heteroaryl group.

The term "oxo" refers to an oxygen atom, which forms a carbonyl when attached to carbon, an N-oxide when attached to nitrogen, and a sulfoxide or sulfone when attached to sulfur.

The term "acyl" refers to an alkylcarbonyl, cycloalkylcarbonyl, arylcarbonyl, heterocyclylcarbonyl, or heteroarylcarbonyl substituent, any of which may be further substituted (e.g., by one or more substituents).

The term "substituents" refers to a group "substituted" on an alkyl, cycloalkyl, alkenyl, alkynyl, heterocyclyl, heterocycloalkenyl, cycloalkenyl, aryl, or heteroaryl group at any atom of that group. Any atom can be substituted. Suitable substituents include, without limitation, alkyl (e.g., C1, C2, C3, C4, C5, C6, C7, C8, C9, C10, C11, C12 straight or branched chain alkyl), cycloalkyl, haloalkyl (e.g., perfluoroalkyl such as $CF_3$), aryl, heteroaryl, aralkyl, heteroaralkyl, heterocyclyl, alkenyl, alkynyl, cycloalkenyl, heterocycloalkenyl, alkoxy, haloalkoxy (e.g., perfluoroalkoxy such as $OCF_3$), halo, hydroxy, carboxy, carboxylate, cyano, nitro, amino, alkyl amino, $SO_3H$, sulfate, phosphate, methylenedioxy (—O—$CH_2$—O— wherein oxygens are attached to vicinal atoms), ethylenedioxy, oxo, thioxo (e.g., C=S), imino (alkyl, aryl, aralkyl), $S(O)_n$alkyl (where n is 0-2), $S(O)_n$ aryl (where n is 0-2), $S(O)_n$ heteroaryl (where n is 0-2), $S(O)_n$ heterocyclyl (where n is 0-2), amine (mono-, di-, alkyl, cycloalkyl, aralkyl, heteroaralkyl, aryl, heteroaryl, and combinations thereof), ester (alkyl, aralkyl, heteroaralkyl, aryl, heteroaryl), amide (mono-, di-, alkyl, aralkyl, heteroaralkyl, aryl, heteroaryl, and combinations thereof), sulfonamide (mono-, di-, alkyl, aralkyl, heteroaralkyl, and combinations thereof). In one aspect, the substituents on a group are independently any one single, or any subset of the aforementioned substituents. In another aspect, a substituent may itself be substituted with any one of the above substituents.

The term "selective" is meant at least 2-fold, 3-fold, 4-fold, 5-fold, 6-fold, or 10-fold greater modulation (e.g., inhibition) of M2 than M1.

The term "activator" as used herein means an agent that (measurably) increases the activity of a pyruvate kinase (e.g., PKM2) or causes pyruvate kinase (e.g., PKM2) activity to increase to a level that is greater than PKM2's basal levels of activity. For example, the activator may mimic the effect caused by a natural ligand (e.g., FBP). The activator effect caused by the agent may be to the same, or to a greater, or to a lesser extent than the activating effect caused by a natural ligand, but the same type of effect is caused. Peptides, nucleic acids, and small molecules may be activators. An agent can be evaluated to determine if it is an activator by measuring either directly or indirectly the activity of the pyruvate kinase when subjected to the agent. The activity of the agent can be measured, for example, against a control substance. In some instances, the activity measured of the agent is for activation of PKM2. The activity of PKM2 can be measured, for example, by monitoring the concentration of a substrate such as ATP or NADH.

The term "inhibitor" as used herein means an agent that measurably slows, stops, decreases or inactivates the enzymatic activity of pyruvate kinase (e.g., PKM2) to decrease to a level that is less than the pyruvate kinase's (e.g., PKM2's) basal levels of activity. Inhibitors of pyruvate kinase (e.g., PKM2) may be peptides or nucleic acids. An agent can be evaluated to determine if it is an inhibitor by measuring either directly or indirectly the activity of the pyruvate kinase when subjected to the agent. The activity of the agent can be measured, for example, against a control substance. In some instances, the activity measured of the agent is for inhibition of PKM2. The activity of PKM2 can be measured, for example, by monitoring the concentration of a substrate such as ATP or NADH.

DETAILED DESCRIPTION

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

Compounds

Described herein are compounds and compositions that modulate PKM2, for example, activate or inhibit PKM2. Compounds that modulate PKM2, e.g., activate or inhibit PKM2, can be used to treat disorders such as neoplastic disorders (e.g., cancer) or fat related disorders (e.g., obesity). Exemplary compounds include the compounds of Formula I, Formula II, Formula III, Formula IV and Formula V described herein. In some embodiments, a compound described herein modulates PKM2 by interacting (e.g., binding) with the FBP binding pocket. For example, a compound described herein can compete with FBP binding in PKM2.

In some embodiments a compound described herein has one or more properties described herein, e.g., one or more of the following properties: it is an allosteric modulator (e.g., inhibitor or activator); it modulates the release of FBP (e.g., inhibits or promotes); it is a modulator (e.g., agonist or antagonist) of FBP, e.g., an agonist which binds with a lower, about the same, or higher affinity than does FBP; it modulates (e.g., inhibits or promotes) the dissolution of tetrameric PKM2; it modulates (e.g., promotes or inhibits) the assembly of tetrameric PKM2; it selectively modulates (e.g., inhibits or activates) PKM2 over at least one other isoform of PK, e.g., it is selective for PKM2 over PKR, PKM1, or PKL; is has an affinity for PKM2 which is greater than its affinity for at least one other isoform of PK, e.g., PKR, PKM1, or PKL.

In another embodiment the activator of PKM2 utilized in the methods and compositions of this invention operates by or has one or more of the following mechanisms or properties:

a. it is an allosteric activator of PKM2;
b. it modulates (e.g., stabilizes or inhibits) the binding of FBP in a binding pocket of PKM2;
c. it modulates (e.g., inhibits or promotes) the release of FBP from a binding pocket of PKM2;
d. it is a modulator (e.g., an agonist or antagonist), e.g., an analog, of FBP, e.g., an agonist which binds PKM2 with a lower, about the same, or higher affinity than does FBP;
e. it modulates (e.g., inhibits or promotes) the dissolution of tetrameric PKM2;
f. it modulates (e.g., inhibits or promotes) the assembly of tetrameric PKM2;
g. it modulates (e.g., stabilizes or inhibits) the tetrameric conformation of PKM2;
h. it modulates (e.g., inhibits or promotes) the binding of a phosphotyrosine containing polypeptide to PKM2;
i. it modulates (e.g., inhibits or promotes) the ability of a phosphotyrosine containing polypeptide to induce release of FBP from PKM2, e.g., by inducing a change in the conformation of PKM2, e.g., in the position of Lys 433, thereby hindering the release of FBP;
k. it binds to or changes the position of Lys 433 relative to the FBP binding pocket;
l. it selectively modulates (e.g., activates or inhibits) PKM2 over at least one other isoform of PK, e.g., it is selective for PKM2 over one or more of PKR, PKM1, or PKL;
m. it has an affinity for PKM2 which is greater than its affinity for at least one other isoform of PK, e.g., PKR, PKM1, or PKL.

A compound described herein may be an activator of PKM2. Exemplary compounds are shown in Table 1. As shown in Table 1, A refers to an activator of PKM2 with an $AC_{50}<1$ μM. B refers to an activator of PKM2 with an $AC_{50}$ between 1 μM and 10 μM. C refers to an activator of PKM2 with an $AC_{50}$ between 10 μM and 50 μM. C refers to an activator of PKM2 with an $AC_{50}$ between 50 μM and 100 μM. D refers to an activator of PKM2 with an $AC_{50}>100$ μM. E refers to an activator of PKM2 that has not been tested.

TABLE 1

| Structure | $AC_{50}$ |
|---|---|
| 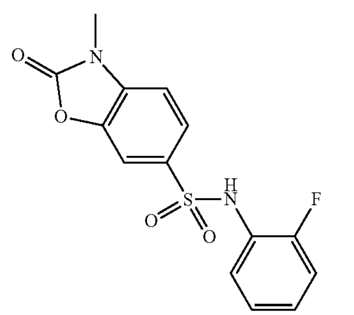 [SMILES: Cn1c(=O)oc2cc(S(=O)(=O)Nc3ccccc3F)ccc21] | E |
| 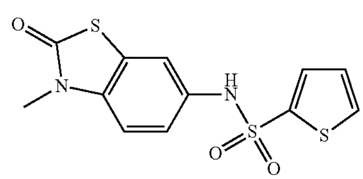 [SMILES: Cn1c(=O)sc2cc(NS(=O)(=O)c3cccs3)ccc21] | C |
| 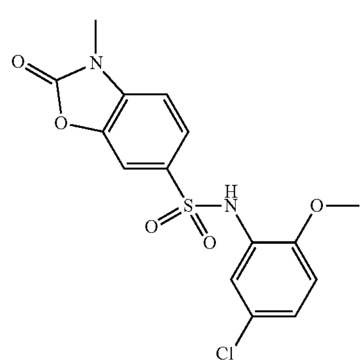 [SMILES: COc1ccc(Cl)cc1NS(=O)(=O)c1ccc2c(c1)oc(=O)n2C] | B |

TABLE 1-continued

| Structure | AC$_{50}$ |
|---|---|
| (benzothiazol-2-one N-methyl, 6-sulfonamide to 5-chloro-2-methoxyphenyl) | C |
| (3-ethyl-6-methylbenzoxazol-2-one, 5-sulfonamide to 4-fluorophenyl) | C |
| (3-ethylbenzoxazol-2-one, 6-sulfonamide to thiophen-2-yl) | D |
| (3-ethylbenzoxazol-2-one, 6-sulfonamide to 2-methoxy-5-chlorophenyl) | E |
| (3,6-dimethylbenzoxazol-2-one, 5-sulfonamide to 3-(chlorocarbonyl)phenyl) | E |

TABLE 1-continued

| Structure | AC$_{50}$ |
|---|---|
| (3,6-dimethylbenzoxazol-2-one, 5-sulfonamide to 4-fluorophenyl) | B |
| (3-methyl-6-chlorobenzoxazol-2-one, 5-sulfonamide to 2-methoxy-5-chlorophenyl) | B |
| (3-ethyl-6-methylbenzoxazol-2-one, 5-sulfonamide to 2-chlorophenyl) | B |
| (3-methyl-6-methylbenzoxazol-2-one, 5-sulfonamide to 2-methoxy-5-chlorophenyl) | D |
| (3-ethylbenzoxazol-2-one, 6-sulfonamide to 2-chlorophenyl) | B |

TABLE 1-continued
| Structure | AC$_{50}$ |
|---|---|
| 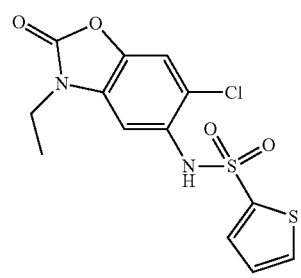 [SMILES: CCn1c(=O)oc2cc(Cl)c(NS(=O)(=O)c3cccs3)cc21] | E |
| 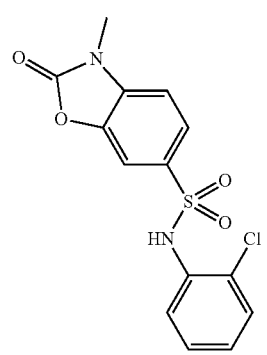 [SMILES: Cn1c(=O)oc2cc(S(=O)(=O)Nc3ccccc3Cl)ccc21] | B |
| 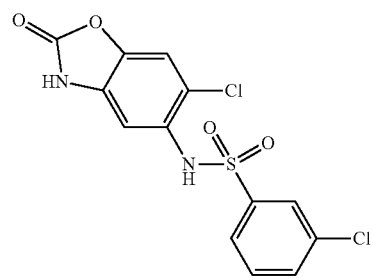 [SMILES: O=c1[nH]c2cc(NS(=O)(=O)c3cccc(Cl)c3)c(Cl)cc2o1] | C |
| 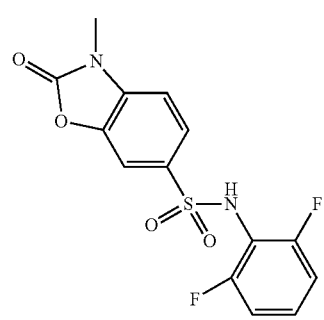 [SMILES: Cn1c(=O)oc2cc(S(=O)(=O)Nc3c(F)cccc3F)ccc21] | B |
| 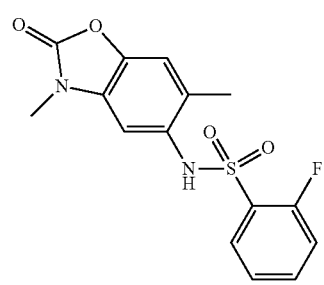 [SMILES: Cc1cc2oc(=O)n(C)c2cc1NS(=O)(=O)c1ccccc1F] | E |combination
TABLE 1-continued
| Structure | AC$_{50}$ |
|---|---|
| 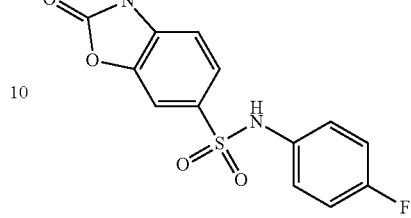 | B |
| 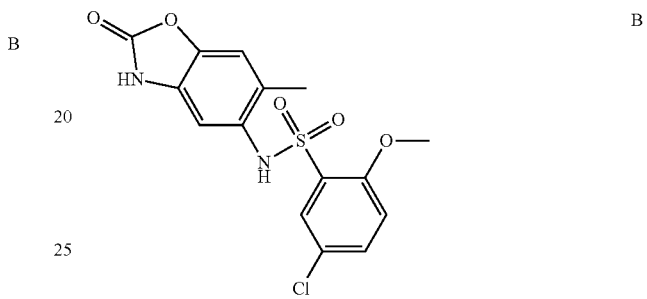 | B |
| 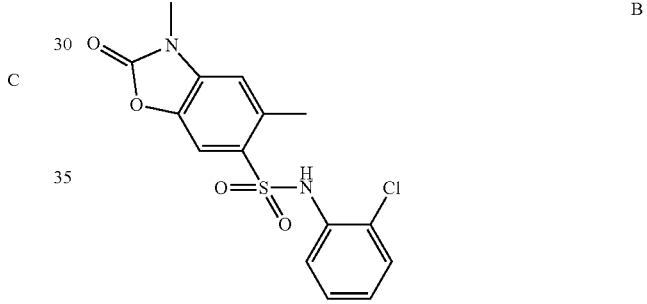 | B |
| 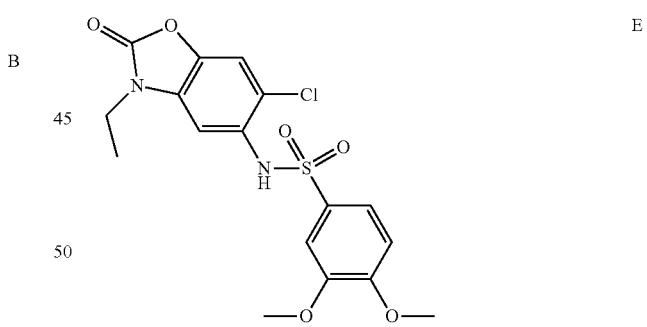 | E |
| 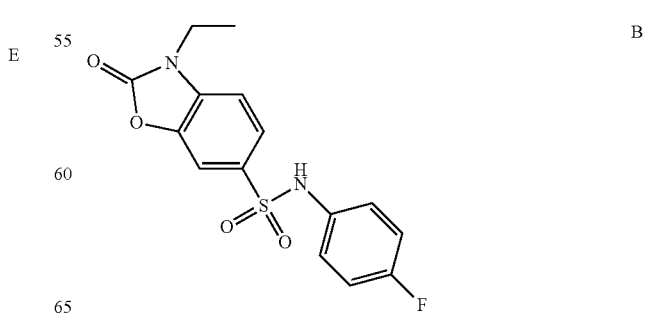 | B |

TABLE 1-continued
| Structure | AC$_{50}$ |
|---|---|
| 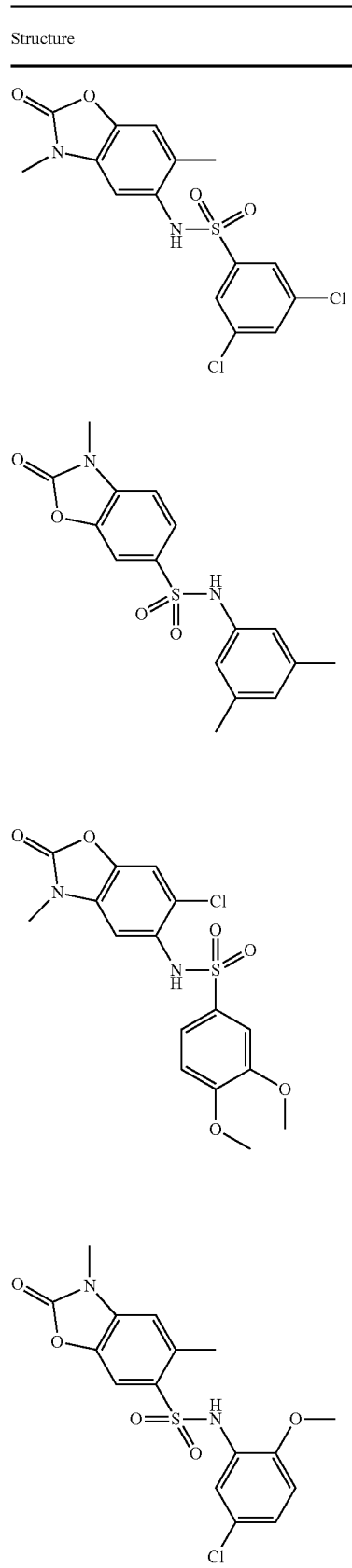 | C |
| 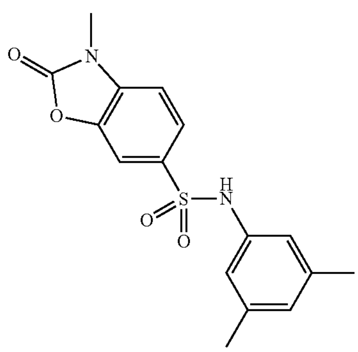 [SMILES: Cc1cc(C)cc(NS(=O)(=O)c2ccc3c(c2)oc(=O)n3C)c1] | A |
| | C |
| 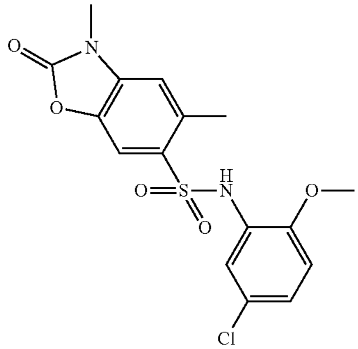 [SMILES: COc1ccc(Cl)cc1NS(=O)(=O)c1cc2oc(=O)n(C)c2cc1C] | B |
TABLE 1-continued
| Structure | AC$_{50}$ |
|---|---|
| 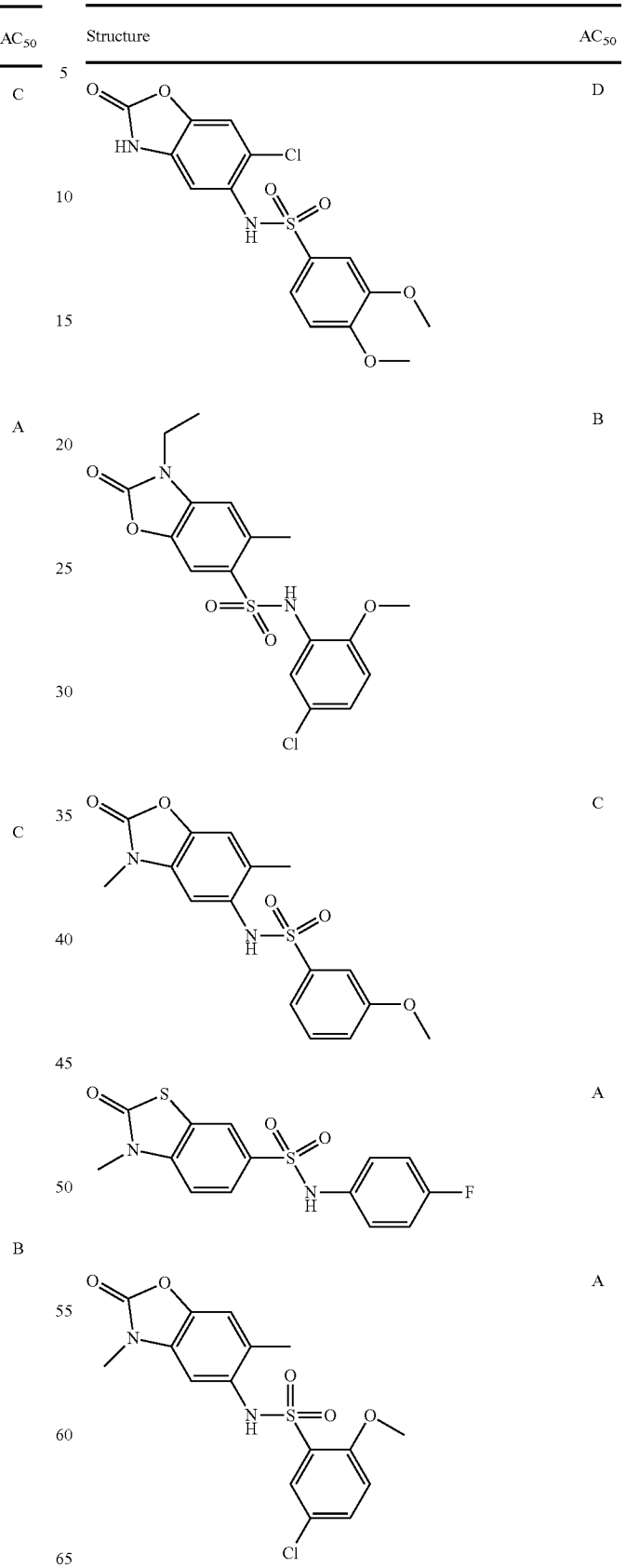 | D |
| 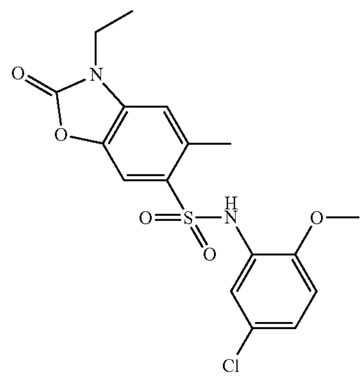 [SMILES: CCn1c(=O)oc2cc(S(=O)(=O)Nc3cc(Cl)ccc3OC)c(C)cc21] | B |
| 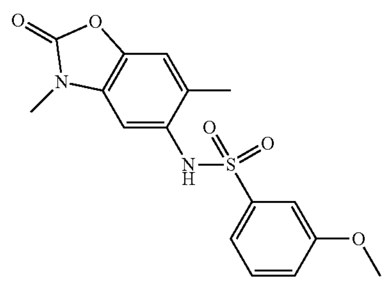 [SMILES: COc1cccc(S(=O)(=O)Nc2cc3c(cc2C)oc(=O)n3C)c1] | C |
| | A |
| | A |

TABLE 1-continued

| Structure | AC₅₀ |
|---|---|
| 6-chloro-3-methyl-N-(2-chlorophenyl)-2-oxo-2,3-dihydrobenzoxazole-5-sulfonamide | B |
| 6-chloro-3-ethyl-N-(5-chloro-2-methoxyphenyl)-2-oxo-2,3-dihydrobenzoxazole-5-sulfonamide | E |
| 6-chloro-N-(2-fluorophenyl)-3-methyl-2-oxo-2,3-dihydrobenzoxazole-5-sulfonamide | B |
| N-(3,4-difluorophenyl)-3,6-dimethyl-2-oxo-2,3-dihydrobenzoxazole-5-sulfonamide | D |
| N-(2-chlorophenyl)-3,6-dimethyl-2-oxo-2,3-dihydrobenzoxazole-5-sulfonamide | B |
| N-(5-chloro-2-methoxyphenyl)-6-fluoro-3-methyl-2-oxo-2,3-dihydrobenzoxazole-5-sulfonamide | C |
| N-(3,5-dimethylphenyl)-3,6-dimethyl-2-oxo-2,3-dihydrobenzoxazole-5-sulfonamide | A |
| N-(2-chlorophenyl)-3,6-dimethyl-2-oxo-2,3-dihydrobenzoxazole-5-sulfonamide | C |
| 6-fluoro-3-methyl-2-oxo-N-phenyl-2,3-dihydrobenzoxazole-5-sulfonamide | A |
| 6-chloro-2-oxo-N-(thiophen-2-yl)sulfonyl-2,3-dihydrobenzoxazole-5-amine | B |

TABLE 1-continued
| Structure | AC$_{50}$ |
|---|---|
| 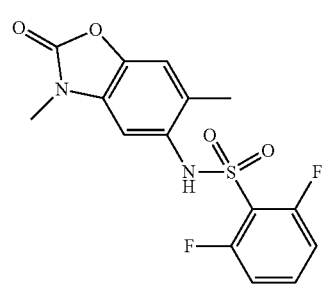 [SMILES: Cc1cc2oc(=O)n(C)c2cc1NS(=O)(=O)c1c(F)cccc1F] | A |
| 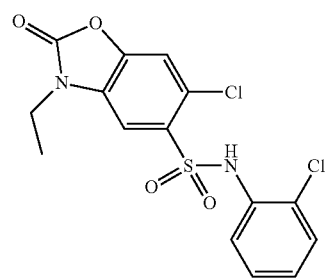 [SMILES: CCn1c(=O)oc2cc(Cl)c(S(=O)(=O)Nc3ccccc3Cl)cc21] | D |
| 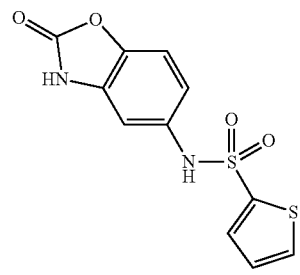 [SMILES: O=c1[nH]c2cc(NS(=O)(=O)c3cccs3)ccc2o1] | D |
| 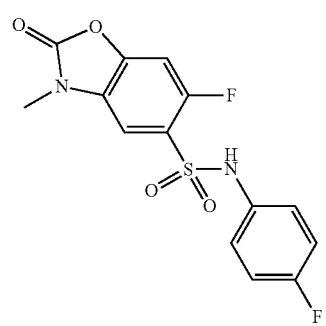 [SMILES: Cn1c(=O)oc2cc(F)c(S(=O)(=O)Nc3ccc(F)cc3)cc21] | C |
| 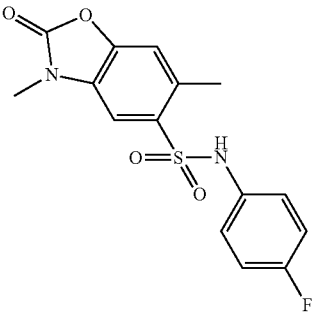 | B |
TABLE 1-continued
| Structure | AC$_{50}$ |
|---|---|
| 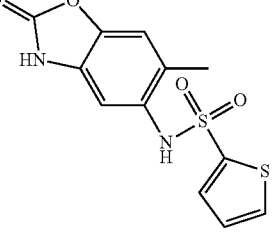 | E |
| 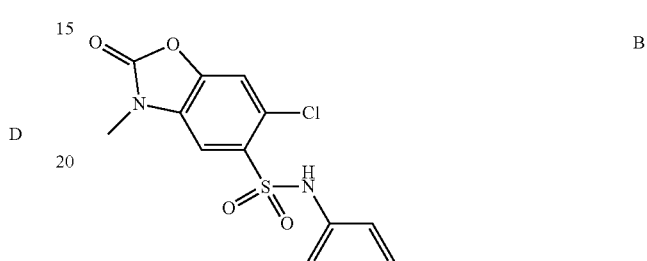 | B |
| 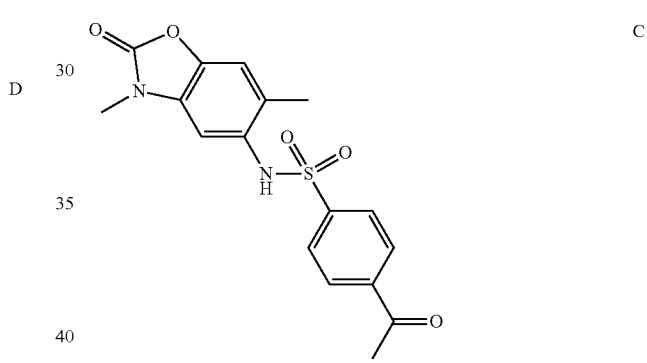 | C |
| 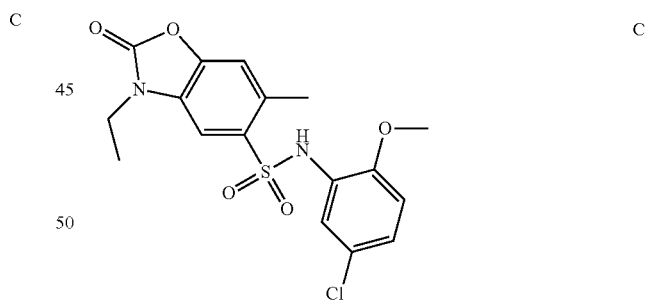 | C |
| 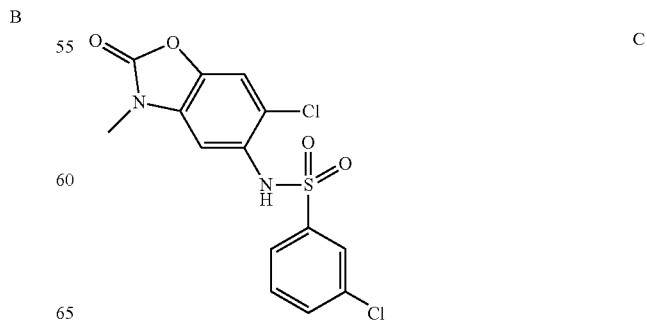 | C |

TABLE 1-continued
| Structure | AC$_{50}$ |
|---|---|
| 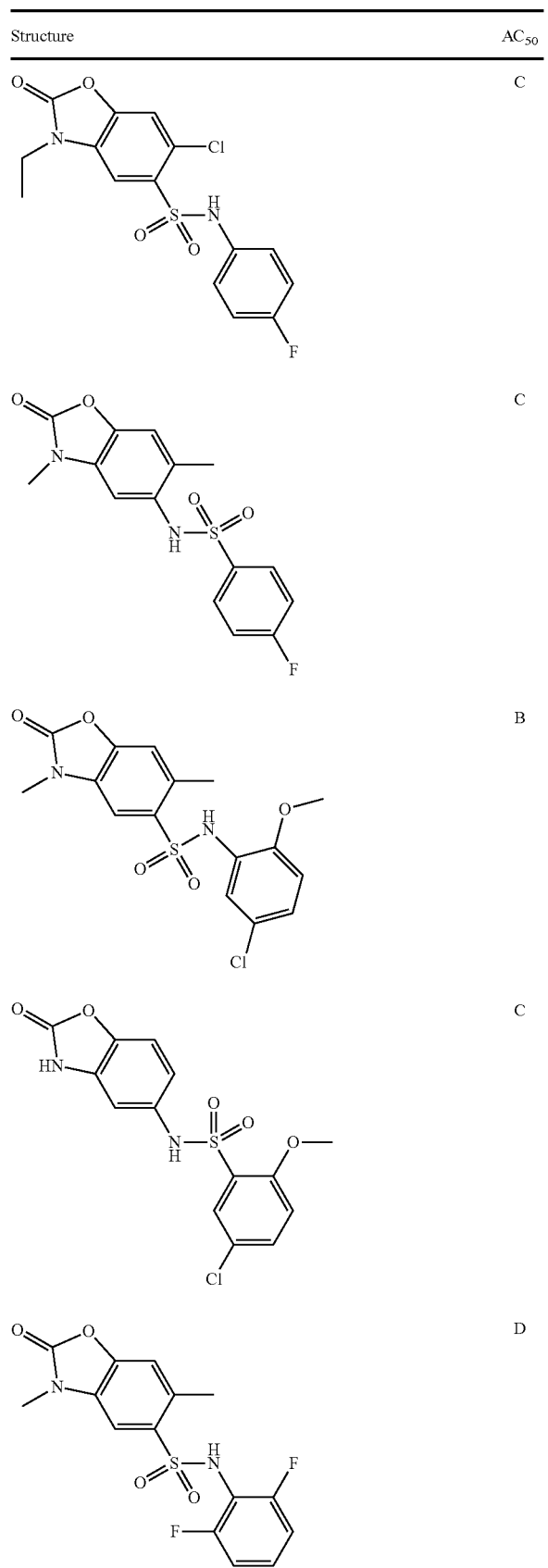 | C |
| | C |
| 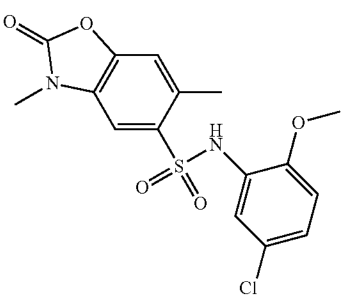 [SMILES: COc1ccc(Cl)cc1NS(=O)(=O)c1cc2c(cc1C)oc(=O)n2C] | B |
| | C |
| 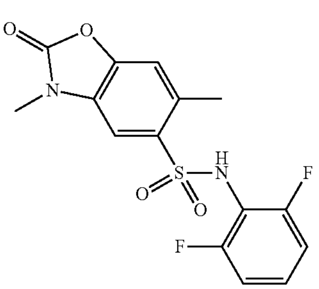 [SMILES: Cc1cc2oc(=O)n(C)c2cc1S(=O)(=O)Nc1c(F)cccc1F] | D |
TABLE 1-continued
| Structure | AC$_{50}$ |
|---|---|
| 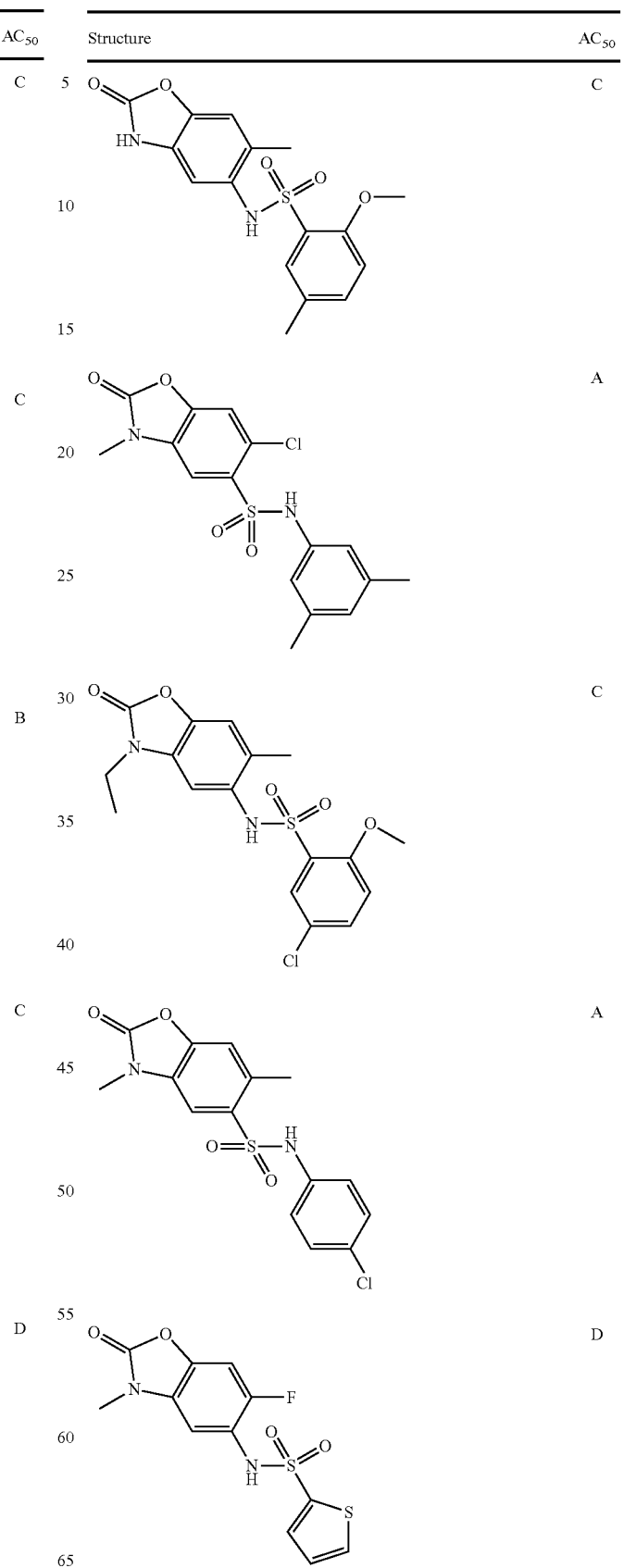 | C |
| | A |
| | C |
| | A |
| 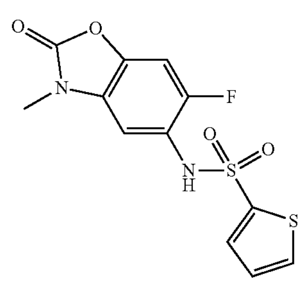 [SMILES: Cn1c(=O)oc2cc(F)c(NS(=O)(=O)c3cccs3)cc21] | D |

TABLE 1-continued

| Structure | AC$_{50}$ |
|---|---|
| (3-ethyl-6-chloro-benzoxazol-2-one-5-yl)sulfonamide of 4-chloroaniline | B |
| (3-ethyl-6-chloro-benzoxazol-2-one-5-yl)sulfonamide of 3-chloroaniline | E |
| (3-methyl-6-fluoro-benzoxazol-2-one-5-yl)sulfonamide of 4-chloroaniline | B |
| (3,6-dimethyl-benzoxazol-2-one-5-yl)sulfonamide of 2-methylaniline | B |
| (3-ethyl-6-methyl-benzoxazol-2-one-5-yl)sulfonamide of 2-chloroaniline | C |
| (3-methyl-6-chloro-benzoxazol-2-one-5-yl)sulfonamide of 2-methoxy-5-methylaniline | B |
| (3-ethyl-6-chloro-benzoxazol-2-one-5-yl)sulfonamide of 2-methoxy-5-chloroaniline | E |
| (6-chloro-benzoxazol-2-one-5-yl)sulfonamide of 2-methoxy-5-methylaniline | E |
| (3,6-dimethyl-benzoxazol-2-one-5-yl)sulfonamide of 2-fluoroaniline | B |
| (3,6-dimethyl-benzoxazol-2-one-5-yl)sulfonamide of 3-chlorobenzenesulfonamide | C |

TABLE 1-continued
| Structure | AC$_{50}$ |
|---|---|
| 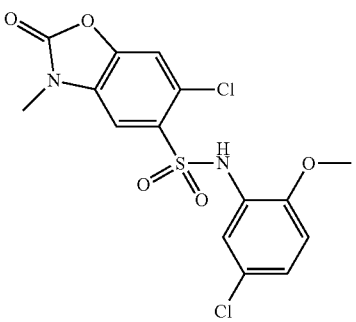 [SMILES: COc1ccc(Cl)cc1NS(=O)(=O)c1cc2c(cc1Cl)oc(=O)n2C] | B |
| 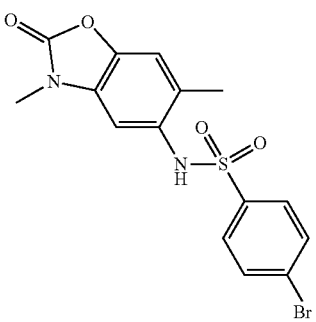 | E |
| 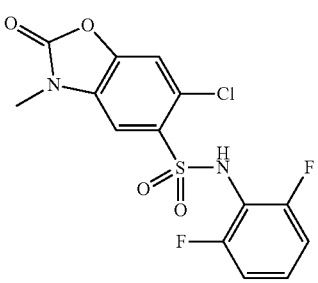 [SMILES: Cn1c(=O)oc2cc(Cl)c(S(=O)(=O)Nc3c(F)cccc3F)cc21] | E |
| 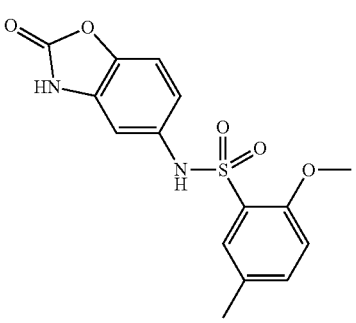 [SMILES: COc1ccc(C)cc1S(=O)(=O)Nc1ccc2oc(=O)[nH]c2c1] | C |
| 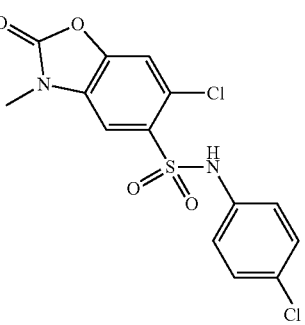 | C |
TABLE 1-continued
| Structure | AC$_{50}$ |
|---|---|
| 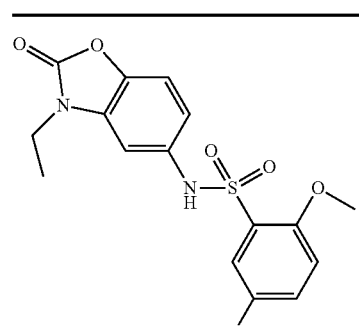 | E |
| 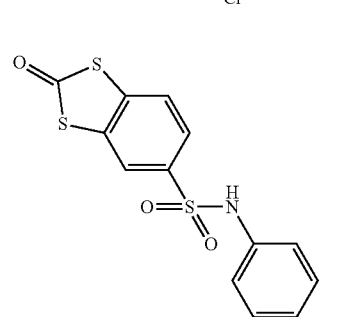 | C |
| 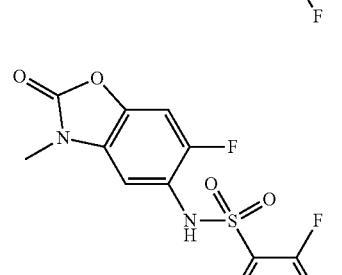 | D |
| 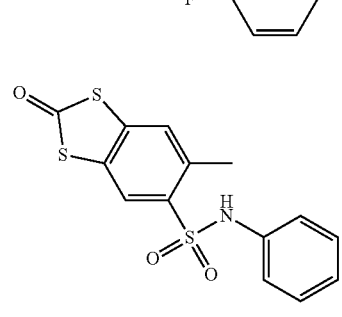 | A |
| 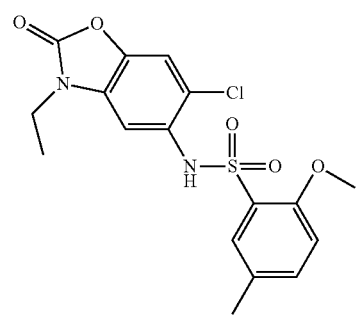 [SMILES: CCn1c(=O)oc2cc(Cl)c(NS(=O)(=O)c3cc(C)ccc3OC)cc21] | E |

TABLE 1-continued

| Structure | AC$_{50}$ |
|---|---|
| (benzodithiol-2-one with methyl and sulfonamide to 3-chloro-5-(trifluoromethyl)pyridin-2-yl) | B |
| (3-methyl-6-chloro-benzoxazol-2-one-5-sulfonamide to thiophen-2-yl) | E |
| (benzodithiol-2-one-5-sulfonamide to 4-chlorophenyl) | B |
| (3-methyl-6-methyl-benzoxazol-2-one-5-sulfonamide to 2,5-dichlorophenyl) | C |
| (benzodithiol-2-one with methyl-sulfonamide to cyclohexyl) | C |
| (3-isopropyl-benzothiazol-2-one-sulfonamide to thiophen-2-yl) | E |
| (benzodithiol-2-one-sulfonamide to 2-methoxy-5-chlorophenyl) | C |
| (3-methyl-benzothiazol-2-one-sulfonamide to 2,6-difluorophenyl) | B |
| (benzodithiol-2-one with methyl-sulfonamide to 4-fluorophenyl) | B |
| (benzothiazol-2-one-sulfonamide to 2,6-difluorophenyl) | C |

TABLE 1-continued
| Structure | AC$_{50}$ |
|---|---|
| 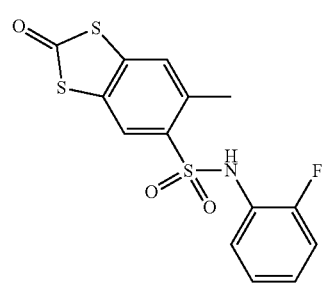 [SMILES: Cc1cc2sc(=O)sc2cc1S(=O)(=O)Nc1ccccc1F] | C |
| 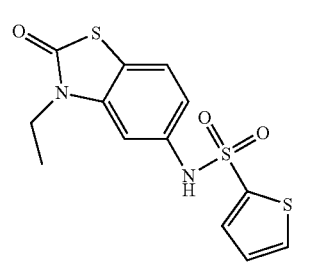 [SMILES: CCn1c(=O)sc2ccc(NS(=O)(=O)c3cccs3)cc21] | C |
| 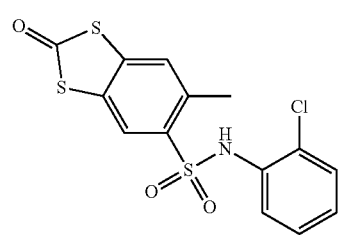 [SMILES: Cc1cc2sc(=O)sc2cc1S(=O)(=O)Nc1ccccc1Cl] | B |
| 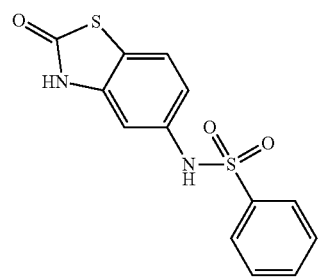 [SMILES: O=c1[nH]c2cc(NS(=O)(=O)c3ccccc3)ccc2s1] | C |
| 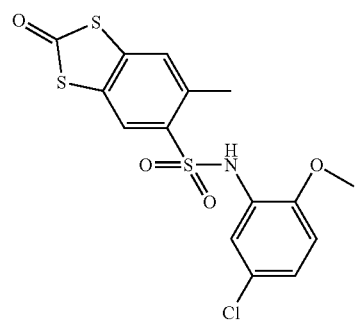 [SMILES: COc1ccc(Cl)cc1NS(=O)(=O)c1cc2sc(=O)sc2cc1C] | B |
| 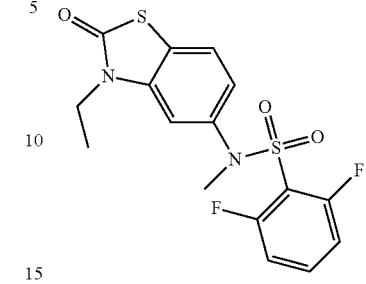 | E |
| 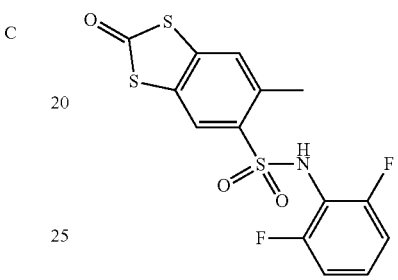 | E |
| 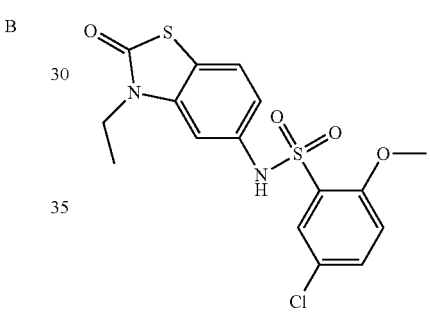 | B |
| 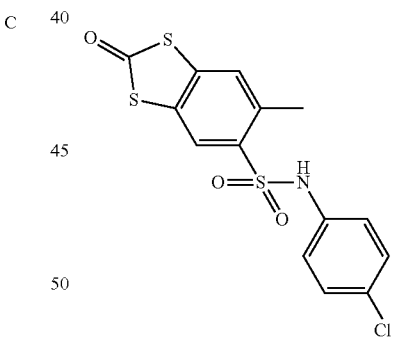 | B |
| 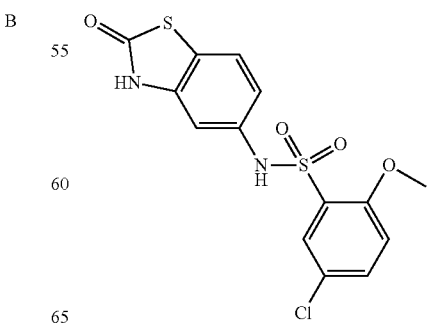 | B |

TABLE 1-continued
| Structure | AC$_{50}$ |
|---|---|
| 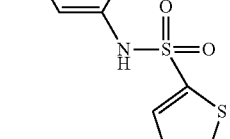 | C |
| 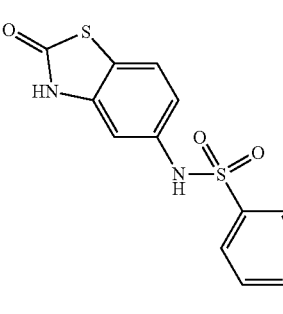 | E |
| 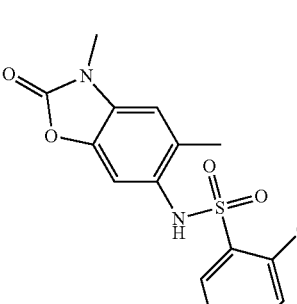 | E |
| 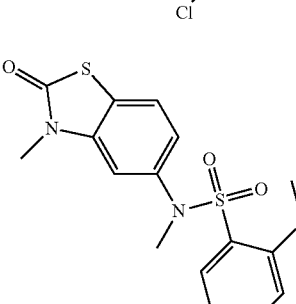 | E |
| 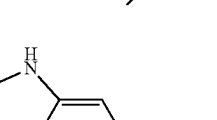 | E |
TABLE 1-continued
| Structure | AC$_{50}$ |
|---|---|
| 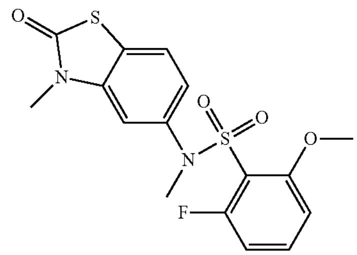 [SMILES: COc1cccc(F)c1S(=O)(=O)N(C)c1ccc2sc(=O)n(C)c2c1] | C |
| | E |
| | B |
| | E |
| | B |

TABLE 1-continued

| Structure | AC$_{50}$ |
|---|---|
| (benzoxazolone with N-methyl, methyl substituent, sulfonamide to 2-methoxy-5-methylphenyl) | E |
| (N-methyl benzothiazolone, sulfonamide to 2-methoxy-5-chlorophenyl) | C |
| (benzoxazolone NH, 6-Cl, sulfonamide to 3,4-dimethoxyphenyl) | E |
| (N-ethyl benzothiazolone, N-methyl sulfonamide to 2-methoxy-5-methylphenyl) | E |
| (N-methyl benzoxazolone, methyl substituent, sulfonamide-NH to 2-thienyl) | C |

TABLE 1-continued

| Structure | AC$_{50}$ |
|---|---|
| (N-ethyl benzothiazolone, sulfonamide to 2,6-difluorophenyl) | B |
| (N-methyl benzoxazolone, methyl substituent, N-methyl sulfonamide to 2-thienyl) | E |
| (benzothiazolone NH, sulfonamide-NH to 2-thienyl) | C |
| (benzoxazolone NH, 6-Cl, sulfonamide-NH to 2-thienyl) | E |
| (N-ethyl benzothiazolone, N-methyl sulfonamide to 2-thienyl) | E |

TABLE 1-continued
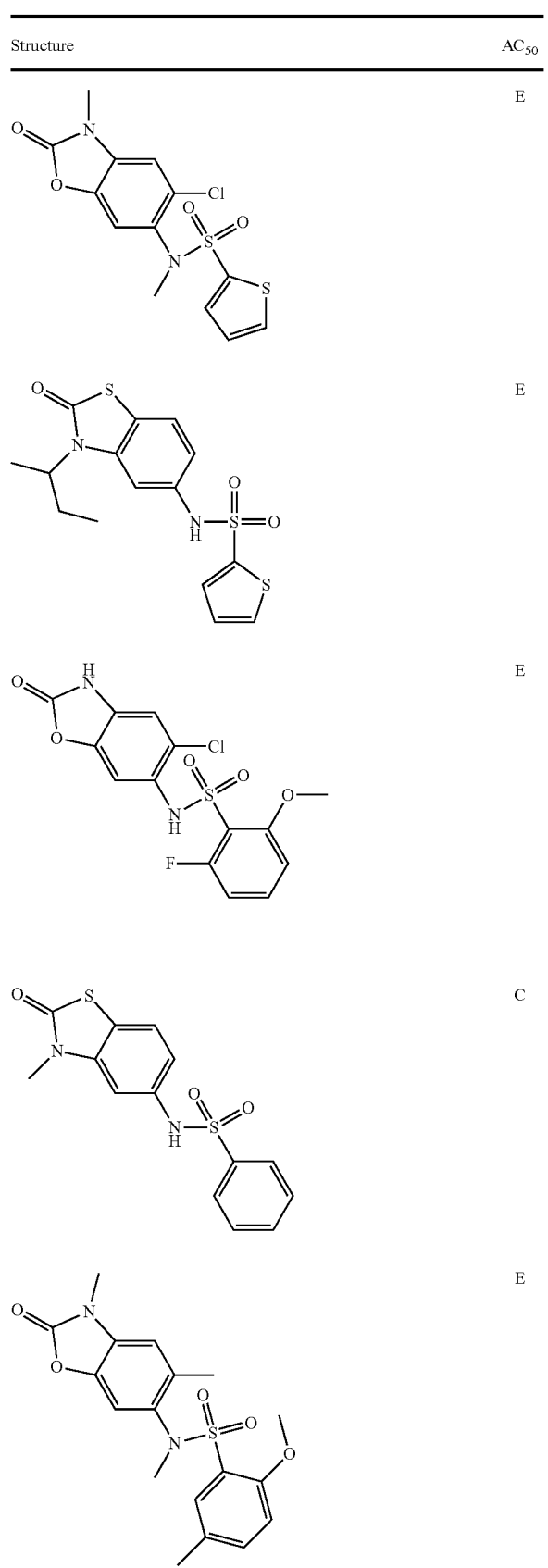

TABLE 1-continued
| Structure | AC₅₀ |
|---|---|
|  | E |
|  | E |
| 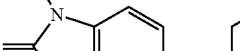 | A |
| 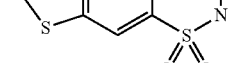 | A |
|  | B |
| 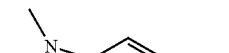 | B |
|  | A |
| 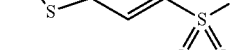 | B |
|  | A |
|  | B |
|  | B |
|  | A |
| 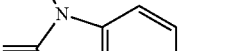 | E |
| | B |

TABLE 1-continued
| Structure | AC$_{50}$ |
|---|---|
| 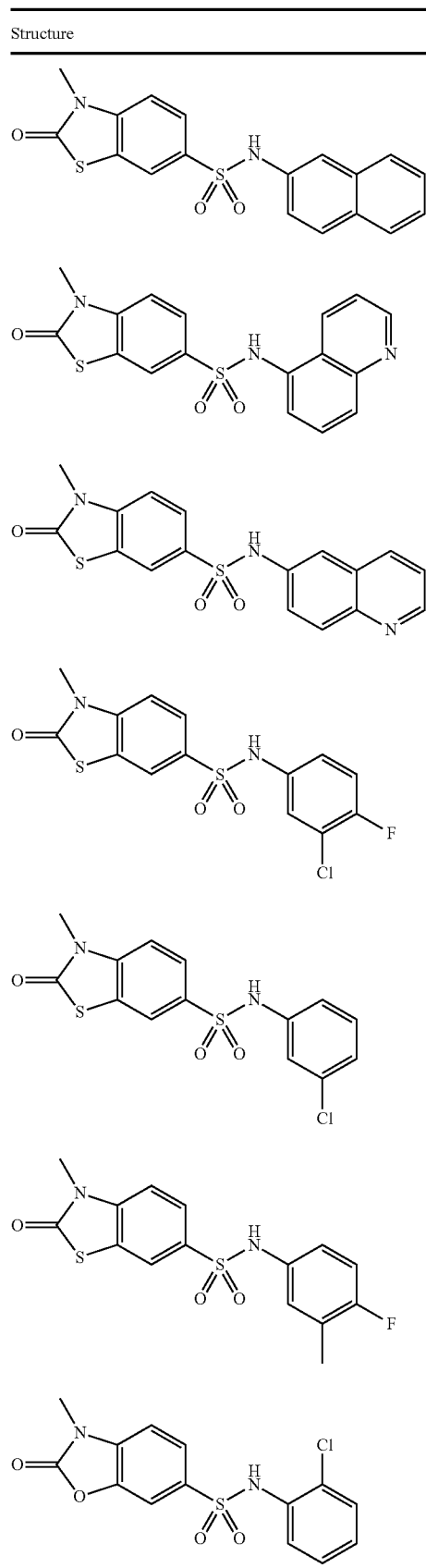 | A |
|  | B |
|  | B |
|  | A |
|  | A |
|  | A |
|  | B |
TABLE 1-continued
| Structure | AC$_{50}$ |
|---|---|
| 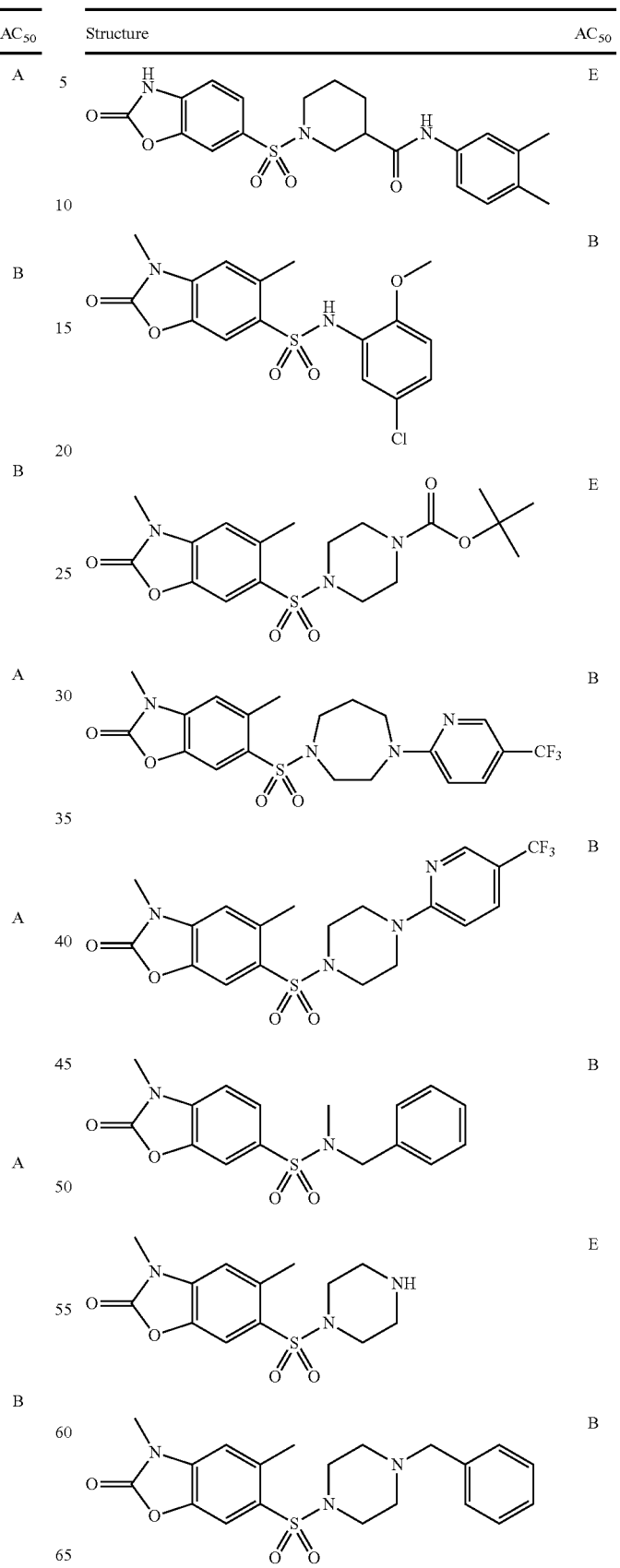 | E |
|  | B |
|  | E |
|  | B |
|  | B |
|  | B |
|  | E |
|  | B |

TABLE 1-continued

| Structure | AC$_{50}$ |
|---|---|
| (3,6-dimethyl-3H-benzooxazol-2-one-5-yl sulfonyl linked to 1,4-diazepane with NH) | E |
| (3,6-dimethyl-3H-benzooxazol-2-one-5-yl sulfonyl linked to 4-benzyl-1,4-diazepane) | E |
| (3-methyl-3H-benzooxazol-2-one-6-yl sulfonamide N-tert-butyl) | D |
| (3-methyl-3H-benzooxazol-2-one-6-yl sulfonamide N-(pyridin-2-yl)) | C |
| (3,6-dimethyl-3H-benzooxazol-2-one-5-yl sulfonamide N-(3,5-dimethylphenyl)) | A |
| (3-benzyl-3H-benzooxazol-2-one-6-yl sulfonamide N-(4-chlorophenyl)) | B |

TABLE 1-continued

| Structure | AC$_{50}$ |
|---|---|
| (3-phenethyl-3H-benzooxazol-2-one-6-yl sulfonamide N-(4-fluorophenyl)) | B |
| (3-benzyl-3H-benzooxazol-2-one-6-yl sulfonamide N-(4-fluorophenyl)) | B |
| (3-methyl-3H-benzooxazol-2-one-6-yl sulfonamide N-(4-chlorophenyl)) | B |
| (3-methyl-3H-benzooxazol-2-one-6-yl sulfonamide N-(2,3-dihydro-1,4-benzodioxin-6-yl)) | B |
| (3-methyl-3H-benzooxazol-2-one-6-yl sulfonamide N-phenyl) | B |
| (3-methyl-3H-benzooxazol-2-one-6-yl sulfonyl piperazine N'-(5-chloro-2-methoxyphenylsulfonyl)) | B |

TABLE 1-continued

| Structure | AC$_{50}$ |
|---|---|
| | B |
| | A |
| | A |
| | B |
| | B |
| | B |

TABLE 1-continued

| Structure | AC$_{50}$ |
|---|---|
| | B |
| 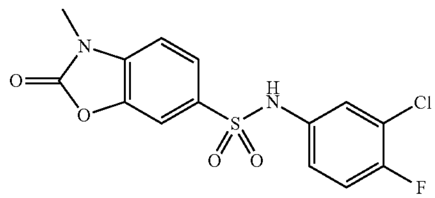 [SMILES: Cn1c(=O)oc2cc(S(=O)(=O)Nc3ccc(Cl)c(Cl)c3)ccc21] | A |
| | B |
| | B |
| | B |
| | B |
| 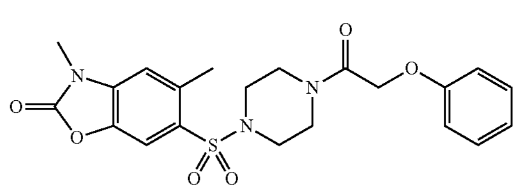 [SMILES: Cc1cc2c(cc1S(=O)(=O)N1CCN(C(=O)COc3ccccc3)CC1)oc(=O)n2C] | D |
| 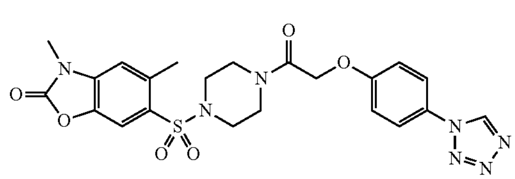 [SMILES: Cc1cc2c(cc1S(=O)(=O)N1CCN(C(=O)COc3ccc(-n4cnnn4)cc3)CC1)oc(=O)n2C] | C |

TABLE 1-continued

| Structure | AC$_{50}$ |
|---|---|
| (3-methyl-2-oxo-6-methyl-benzoxazole-5-sulfonyl)-piperazine-N-sulfonyl-2,3-dihydro-benzo[1,4]dioxine | A |
| (3-methyl-2-oxo-6-methyl-benzoxazole-5-sulfonyl)-piperazine-N-sulfonyl-(2-methoxy-5-chloro-phenyl) | E |
| (3-methyl-2-oxo-benzoxazole-5-sulfonyl)-piperazine-N-sulfonyl-2,3-dihydro-benzo[1,4]dioxine | A |
| 3-methyl-2-oxo-benzoxazole-5-sulfonamide-N-(3,5-dimethoxyphenyl) | A |
| 3-methyl-2-oxo-benzoxazole-5-sulfonamide-N-(benzo[1,3]dioxol-5-yl) | A |
| 3-methyl-2-oxo-benzoxazole-5-sulfonamide-N-(3,4-dimethylphenyl) | A |
| 3-methyl-2-oxo-benzoxazole-5-sulfonamide-N-(3-methyl-4-chloro-phenyl) | A |

TABLE 1-continued

| Structure | AC$_{50}$ |
|---|---|
| 3-methyl-2-oxo-benzoxazole-5-sulfonamide-N-(3-trifluoromethyl-phenyl) | B |
| 3-methyl-2-oxo-benzoxazole-5-sulfonamide-N-(3-chloro-phenyl) | A |
| 3-methyl-2-oxo-benzoxazole-5-sulfonamide-N-(3,4-difluoro-phenyl) | A |
| 3-methyl-2-oxo-benzoxazole-5-sulfonamide-N-(3-bromo-4-trifluoromethoxy-phenyl) | B |
| 3-methyl-2-oxo-benzoxazole-5-sulfonamide-N-(3-chloro-4-trifluoromethoxy-phenyl) | B |
| 3-methyl-2-oxo-benzoxazole-5-sulfonamide-N-(3-chloro-5-fluoro-phenyl) | A |
| 3-methyl-2-oxo-benzoxazole-5-sulfonamide-N-(3,5-dichloro-phenyl) | A |

TABLE 1-continued

| Structure | AC$_{50}$ |
|---|---|
| (3-methyl-2-oxo-2,3-dihydrobenzoxazol-6-yl)sulfonyl-NH-(3-ethylphenyl) | A |
| (3-methyl-2-oxo-2,3-dihydrobenzoxazol-6-yl)sulfonyl-NH-(4-((2-methoxy-5-methylphenyl)sulfonylamino)phenyl) | B |
| (3-methyl-2-oxo-2,3-dihydrobenzoxazol-6-yl)sulfonyl-NH-cyclohexyl | B |
| (3-methyl-2-oxo-2,3-dihydrobenzoxazol-6-yl)sulfonyl-NH-(4-((2,6-difluorophenyl)sulfonylamino)phenyl) | E |
| (3-methyl-2-oxo-2,3-dihydrobenzoxazol-6-yl)sulfonyl-NH-(naphthalen-1-yl) | B |
| (3-methyl-2-oxo-2,3-dihydrobenzoxazol-6-yl)sulfonyl-NH-(naphthalen-2-yl) | B |
| (3-methyl-2-oxo-2,3-dihydrobenzoxazol-6-yl)sulfonyl-NH-(quinolin-6-yl) | B |
| (3-methyl-2-oxo-2,3-dihydrobenzoxazol-6-yl)sulfonyl-NH-(quinolin-5-yl) | C |
| (3-methyl-2-oxo-2,3-dihydrobenzoxazol-6-yl)sulfonyl-NH-(3-CF$_3$-4-F-phenyl) | A |
| (3-methyl-2-oxo-2,3-dihydrobenzoxazol-6-yl)sulfonyl-NH-(1-((3-methyl-2-oxo-2,3-dihydrobenzoxazol-7-yl)sulfonyl)-1H-benzimidazol-6-yl) | B |
| (3-(2-methoxyethyl)-2-oxo-2,3-dihydrobenzoxazol-6-yl)sulfonyl-NH-(3-chlorophenyl) | A |
| (3-(2-methoxyethyl)-2-oxo-2,3-dihydrobenzoxazol-6-yl)sulfonyl-NH-(3-chloro-4-fluorophenyl) | A |
| (3-(2-methoxyethyl)-2-oxo-2,3-dihydrobenzoxazol-6-yl)sulfonyl-NH-(3-methyl-4-fluorophenyl) | A |

TABLE 1-continued

| Structure | AC$_{50}$ |
|---|---|
| (structure) | A |
| (structure) | A |
| (structure) | A |
| (structure) | A |
| (structure) | A |
| (structure) | A |

TABLE 1-continued

| Structure | AC$_{50}$ |
|---|---|
| (structure) | B |
| (structure) | A |
| (structure) | B |
| (structure) | B |
| (structure) | D |

TABLE 1-continued

| Structure | AC$_{50}$ |
|---|---|
| (benzoxazolone-F, SO2NH-phenyl) | B |
| (benzoxazolone-Cl, SO2NH-2-F-phenyl) | B |
| (benzoxazolone-F, SO2NH-2,6-diF-phenyl) | D |
| (benzoxazolone-Me, SO2-piperazine-N-(5-CF3-pyridin-2-yl)) | B |
| (benzoxazolone, SO2NH-3,5-diMe-phenyl) | A |
| (benzoxazolone-Me, SO2-homopiperazine-N-(5-CF3-pyridin-2-yl)) | B |
| (benzoxazolone-F, SO2-piperazine-N-SO2-2,3-dihydrobenzo[1,4]dioxin-6-yl) | A |
| (benzoxazolone-F, SO2-piperazine-N-SO2-(2-OMe-5-Cl-phenyl)) | A |
| (benzoxazolone-F, SO2-piperazine-N-SO2-(2,6-diF-phenyl)) | A |
| (benzoxazolone-Me, SO2NH-phenyl-NHSO2-(2-OMe-5-Cl-phenyl)) | D |
| (benzoxazolone-Me, SO2NH-3,5-diF-phenyl) | B |
| (benzoxazolone-Me, SO2NH-3-F-4-Me-phenyl) | A |
| (benzoxazolone-Me, SO2NH-3-Cl-4-OCF3-phenyl) | B |
| (benzoxazolone-Me, SO2NH-3,4-diMe-phenyl) | A |
| (benzoxazolone-Me, SO2NH-benzo[1,3]dioxol-5-yl) | A |
| (benzoxazolone-Me, SO2NH-3,5-diOMe-phenyl) | B |

TABLE 1-continued

| Structure | AC$_{50}$ |
|---|---|
| (benzoxazolone-methyl, 6-F, sulfonamide-N-(3,5-dimethylphenyl)) | A |
| (benzoxazolone-methyl, 6-methyl, sulfonamide-N-(4-acetamidophenyl)) | D |
| (benzoxazolone-methyl, 6-methyl, sulfonamide-N-(3-methyl-4-chlorophenyl)) | A |
| (benzoxazolone-methyl, 6-methyl, sulfonamide-N-(3-chlorophenyl)) | A |
| (benzoxazolone-methyl, 6-methyl, sulfonamide-N-(3-CF$_3$-4-chlorophenyl)) | B |
| (benzoxazolone-methyl, 6-methyl, sulfonamide-N-(3,4-dichlorophenyl)) | B |
| (benzoxazolone-methyl, 6-methyl, sulfonamide-N-(3-F-4-chlorophenyl)) | B |
| (benzoxazolone-methyl, 6-methyl, sulfonamide-N-(3-chloro-4-fluorophenyl)) | A |

TABLE 1-continued

| Structure | AC$_{50}$ |
|---|---|
| (benzoxazolone-methyl, 6-methyl, sulfonamide-N-(3-chloro-5-fluorophenyl)) | B |
| (benzoxazolone-methyl, 6-methyl, sulfonamide-N-(3-ethylphenyl)) | A |
| (benzoxazolone-(2-methoxyethyl), 6-methyl, sulfonamide-N-(3-methyl-4-fluorophenyl)) | B |
| (benzoxazolone-methyl, 6-methyl, sulfonyl-piperazine-C(O)CH$_2$-(4-CF$_3$-phenyl)) | D |
| (benzoxazolone-(2-methoxyethyl), 6-methyl, sulfonamide-N-(3-chloro-4-fluorophenyl)) | B |

The compounds described herein can be made using a variety of synthetic techniques. In some embodiments, a compound described herein may be available from a commercial source. Schemes 1 and 2 below depict representative syntheses of certain compounds described herein. Scheme 3 represents the synthesis of a compound described herein.

Scheme 1.

$$H_2N-\text{(benzoxazole-X=Z,Y)}-(R^2)_n + \text{B}-(R^1)_m-SO_2Cl \xrightarrow[\text{CH}_2\text{Cl}_2]{\text{base}}$$

$$\text{B}(R^1)_m-SO_2-NH-\text{(benzoxazole-X=Z,Y)}-(R^2)_n$$

Scheme 2.

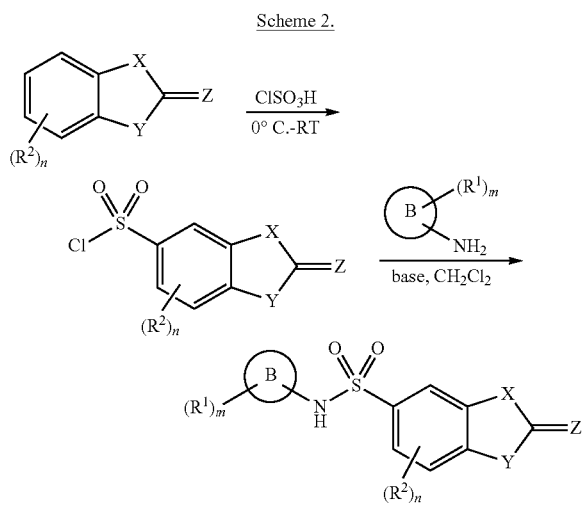

Scheme 3.

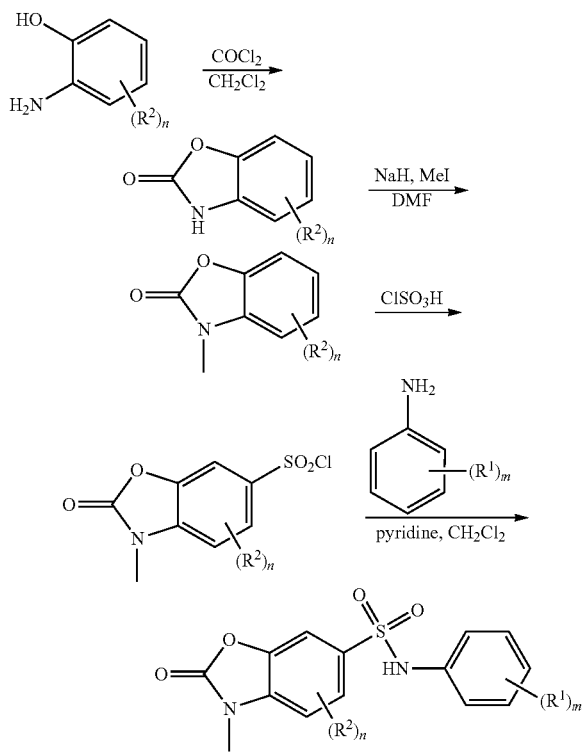

As can be appreciated by the skilled artisan, methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The compounds of this invention may contain one or more asymmetric centers and thus occur as racemates and racemic mixtures, single enantiomers, individual diastereomers and diastereomeric mixtures. All such isomeric forms of these compounds are expressly included in the present invention. The compounds of this invention may also contain linkages (e.g., carbon-carbon bonds) or substituents that can restrict bond rotation, e.g. restriction resulting from the presence of a ring or double bond. Accordingly, all cis/trans and E/Z isomers are expressly included in the present invention.

The compounds of this invention may also be represented in multiple tautomeric forms, in such instances, the invention expressly includes all tautomeric forms of the compounds described herein, even though only a single tautomeric form may be represented (e.g., alkylation of a ring system may result in alkylation at multiple sites, the invention expressly includes all such reaction products). All such isomeric forms of such compounds are expressly included in the present invention. All crystal forms of the compounds described herein are expressly included in the present invention.

The compounds of this invention include the compounds themselves, as well as their salts and their prodrugs, if applicable. A salt, for example, can be formed between an anion and a positively charged substituent (e.g., amino) on a compound described herein. Suitable anions include chloride, bromide, iodide, sulfate, nitrate, phosphate, citrate, methanesulfonate, trifluoroacetate, and acetate. Likewise, a salt can also be formed between a cation and a negatively charged substituent (e.g., carboxylate) on a compound described herein. Suitable cations include sodium ion, potassium ion, magnesium ion, calcium ion, and an ammonium cation such as tetramethylammonium ion. Examples of prodrugs include esters and other pharmaceutically acceptable derivatives, which, upon administration to a subject, are capable of providing active compounds.

The compounds of this invention may be modified by appending appropriate functionalities to enhance selected biological properties, e.g., targeting to a particular tissue. Such modifications are known in the art and include those which increase biological penetration into a given biological compartment (e.g., blood, lymphatic system, central nervous system), increase oral availability, increase solubility to allow administration by injection, alter metabolism and alter rate of excretion.

In an alternate embodiment, the compounds described herein may be used as platforms or scaffolds that may be utilized in combinatorial chemistry techniques for preparation of derivatives and/or chemical libraries of compounds. Such derivatives and libraries of compounds have biological activity and are useful for identifying and designing compounds possessing a particular activity. Combinatorial techniques suitable for utilizing the compounds described herein are known in the art as exemplified by Obrecht, D. and Villalgrodo, J. M., *Solid-Supported Combinatorial and Parallel Synthesis of Small-Molecular-Weight Compound Libraries*, Pergamon-Elsevier Science Limited (1998), and include those such as the "split and pool" or "parallel" synthesis techniques, solid-phase and solution-phase techniques, and encoding techniques (see, for example, Czarnik, A. W., *Curr. Opin. Chem. Bio.*, (1997) 1, 60. Thus, one embodiment relates to a method of using the compounds described herein for generating derivatives or chemical libraries comprising: 1) providing a body comprising a plurality of wells; 2) providing one or more compounds identified by methods described herein in each well; 3) providing an additional one or more chemicals in each well; 4) isolating the resulting one or more products from each well. An alternate embodiment relates to a method of using the compounds described herein for generating derivatives or chemical libraries comprising: 1) providing one or more compounds described herein attached to a solid support; 2) treating the one or more compounds identified by methods described herein attached to a solid support with one or more additional chemicals; 3) isolating the resulting one or more products from the solid support. In the methods described above, "tags" or identifier or labeling moieties may be attached to and/or detached from the compounds described herein or their derivatives, to facilitate tracking, identification or isolation of the desired products or their intermediates. Such moieties are known in the art. The chemicals used in the aforementioned methods may include, for example, solvents, reagents, catalysts, protecting group and deprotecting group reagents and the like. Examples of such chemicals are those that appear in the various synthetic and protecting group chemistry texts and treatises referenced herein.

Methods of Evaluating Compounds

The compounds described herein can be evaluated for ability to modulate PKM2 (e.g., activate or inhibit PKM2) by methods known in the art. Exemplary methods include contacting the compound with a cell-based assay which allows assessment of the ability to modulate (e.g., activate or inhibit) PKM2. E.g., the candidate compound can be contacted with a cell and measuring the consumption of oxygen or production of lactate. A change in cellular phosphoenolpyruvate, a change in glycerol-phosphate, a change in ribose or deoxyribose, a change in lipid synthesis, or a change in glucose conversion to lipid or nucleic acids or amino acids or protein can also be used to evaluate a compound for its ability to modulate PKM2 (e.g., activate or inhibit PKM2). The evaluation could also include measuring a change in pyruvate or a determination of an alteration in mitochondrial membrane potential, e.g., as measured by fluorescent potentiometric dyes.

PKM1 and PKM2 for use in the screening method may be produced by any method known in the art for expression of recombinant proteins. For example, nucleic acids that encode the desired polypeptide may be introduced into various cell types or cell-free systems for expression. Eukaryotic (e.g., COS, HEK293T, CHO, and NIH cell lines) and prokaryotic (e.g., *E. coli*) expression systems may be generated in which a PKM sequence is introduced into a plasmid or other vector, which is then used to transform living cells. Constructs in which the PKM cDNA contains the entire open reading frame, or biologically active fragment thereof, are inserted in the correct orientation into an expression plasmid and may be used for protein expression. Prokaryotic and eukaryotic expression systems allow for the expression and recovery of fusion proteins in which the PKM protein is covalently linked to a tag molecule on either the amino terminal or carboxy terminal side, which facilitates identification and/or purification. Examples of tags that can be used include hexahistidine, HA, FLAG, and c-myc epitope tags. An enzymatic or chemical cleavage site can be engineered between the PKM protein and the tag molecule so that the tag can be removed following purification.

The activity of the PKM enzyme measured in the screening assay may be measured by, e.g., monitoring the concentration of a substrate (e.g., ATP or NADH) present in the reaction mixture. Pyruvate, produced by the enzymatic activity of pyruvate kinase, is converted into lactate by lactate dehydrogenase, which requires the consumption of NADH (NADH→NAD+). Thus, the activity of PKM2 can be indirectly measured by monitoring the consumption of NADH through, e.g., fluorescence assays. Additionally, the activity of the PKM2 enzyme can be directly monitored by measuring the production of ATP, as ATP is produced when phosphoenolpyruvate is converted to pyruvate. Methods for monitoring the amount of substrate in a reaction mixture include, e.g., absorbance, fluorescence, Raman scattering, phosphorescence, luminescence, luciferase assays, and radioactivity.

The screening procedure requires the presence of specific components in the reaction mixture. Components utilized in the assay include, e.g., a nucleoside diphosphate (e.g., ADP), phosphoenolpyruvate, NADH, lactate dehydrogenase, FBP, a reducing agent (e.g., dithiothreitol), a detergent (e.g., Brij 35), glycerol, and a solvent (e.g., DMSO). Exemplary reaction conditions are found in Table 2.

TABLE 2

| Component of Reaction Condition | Amount in Inhibition Assay | Amount in Activation Assay |
| --- | --- | --- |
| ADP | 0.1-5.0 mM | 0.1-5.0 mM |
| Phosphoenolpyruvate | 0.1-5.0 mM | 0.1-5.0 mM |
| NADH | 10-1000 µM | 10-1000 µM |
| Lactate dehydrogenase | 0.1-10 units | 0.1-10 units |
| Fructose-1,6-bisphosphate | 1-500 µM | 0 |
| DTT | 0.1-50 mM | 0.1-50 mM |
| Brij 35 | 0.01-1% | 0.01-1% |
| Glycerol | 0.1-10% | 0.1-10% |
| Pyruvate Kinase M2 (used for screen) | 1-100 pg | 1-100 pg |
| DMSO | 1-10% | 1-10% |

Candidate inhibitory compounds are chosen if they demonstrate specificity for PKM2 and inhibition of the PKM2 enzyme greater than 10, 15, 20, 25, 30, 35, 40, 45, 50, 55, 60, 65, 70, 75, 80, 85, 90, 95, 99, or 99.9%.

Candidate activator compounds are chosen if they demonstrate specificity and activation of PKM2 enzyme in the absence of FBP to a level greater than that of 10, 15, 20, 25, 30, 35, 40, 45, 50, 55, 60, 65, 70, 75, 80, 85, 90, 95, 99, or 100% in the presence of FBP. Furthermore, specific candidate activators of PKM2 can be evaluated in the presence or absence of a phosphotyrosine peptide. Phosphotyrosine peptide binding to PKM2 leads to a dissociation of FBP from PKM2 and conformational changes of PKM2 from an active, tetrameric form to an inactive form. Compounds that bind to PKM2 and lock the enzyme in the active confirmation even in the presence of a phosphotyrosine peptide will lead to the loss of allosteric control of PKM2 needed for shunting the biochemical intermediates from glycolysis into biosynthesis of other intermediates. This, in turn, will lead to inhibition of growth of cancer cells, activated immune cells and fat cells.

Methods of Treatment

The compounds and compositions described herein can be administered to cells in culture, e.g. in vitro or ex vivo, or to a subject, e.g., in vivo, to treat, prevent, and/or diagnose a variety of disorders, including those described herein below.

As used herein, the term "treat" or "treatment" is defined as the application or administration of a compound, alone or in combination with, a second compound to a subject, e.g., a patient, or application or administration of the compound to an isolated tissue or cell, e.g., cell line, from a subject, e.g., a patient, who has a disorder (e.g., a disorder as described herein), a symptom of a disorder, or a predisposition toward a disorder, with the purpose to cure, heal, alleviate, relieve, alter, remedy, ameliorate, improve or affect the disorder, one or more symptoms of the disorder or the predisposition toward the disorder (e.g., to prevent at least one symptom of the disorder or to delay onset of at least one symptom of the disorder).

As used herein, an amount of a compound effective to treat a disorder, or a "therapeutically effective amount" refers to an amount of the compound which is effective, upon single or multiple dose administration to a subject, in treating a cell, or in curing, alleviating, relieving or improving a subject with a disorder beyond that expected in the absence of such treatment.

As used herein, an amount of a compound effective to prevent a disorder, or "a prophylactically effective amount" of the compound refers to an amount effective, upon single- or multiple-dose administration to the subject, in preventing or delaying the occurrence of the onset or recurrence of a disorder or a symptom of the disorder.

As used herein, the term "subject" is intended to include human and non-human animals. Exemplary human subjects include a human patient having a disorder, e.g., a disorder described herein or a normal subject. The term "non-human animals" of the invention includes all vertebrates, e.g., non-mammals (such as chickens, amphibians, reptiles) and mammals, such as non-human primates, domesticated and/or agriculturally useful animals, e.g., sheep, dog, cat, cow, pig, etc.

Neoplastic Disorders

A compound or composition described herein can be used to treat a neoplastic disorder. A "neoplastic disorder" is a disease or disorder characterized by cells that have the capacity for autonomous growth or replication, e.g., an abnormal state or condition characterized by proliferative cell growth. Exemplary neoplastic disorders include: carcinoma, sarcoma, metastatic disorders (e.g., tumors arising from prostate, colon, lung, breast and liver origin), hematopoietic neoplastic disorders, e.g., leukemias, metastatic tumors. Prevalent cancers include: breast, prostate, colon, lung, liver, and pancreatic cancers. Treatment with the compound may be in an amount effective to ameliorate at least one symptom of the neoplastic disorder, e.g., reduced cell proliferation, reduced tumor mass, etc.

The disclosed methods are useful in the prevention and treatment of cancer, including for example, solid tumors, soft tissue tumors, and metastases thereof. The disclosed methods are also useful in treating non-solid cancers. Exemplary solid tumors include malignancies (e.g., sarcomas, adenocarcinomas, and carcinomas) of the various organ systems, such as those of lung, breast, lymphoid, gastrointestinal (e.g., colon), and genitourinary (e.g., renal, urothelial, or testicular tumors) tracts, pharynx, prostate, and ovary. Exemplary adenocarcinomas include colorectal cancers, renal-cell carcinoma, liver cancer, non-small cell carcinoma of the lung, and cancer of the small intestine.

Exemplary cancers described by the national cancer institute include: Acute Lymphoblastic Leukemia, Adult; Acute Lymphoblastic Leukemia, Childhood; Acute Myeloid Leukemia, Adult; Adrenocortical Carcinoma; Adrenocortical Carcinoma, Childhood; AIDS-Related Lymphoma; AIDS-Related Malignancies; Anal Cancer; Astrocytoma, Childhood Cerebellar; Astrocytoma, Childhood Cerebral; Bile Duct Cancer, Extrahepatic; Bladder Cancer; Bladder Cancer, Childhood; Bone Cancer, Osteosarcoma/Malignant Fibrous Histiocytoma; Brain Stem Glioma, Childhood; Brain Tumor, Adult; Brain Tumor, Brain Stem Glioma, Childhood; Brain Tumor, Cerebellar Astrocytoma, Childhood; Brain Tumor, Cerebral Astrocytoma/Malignant Glioma, Childhood; Brain Tumor, Ependymoma, Childhood; Brain Tumor, Medulloblastoma, Childhood; Brain Tumor, Supratentorial Primitive Neuroectodermal Tumors, Childhood; Brain Tumor, Visual Pathway and Hypothalamic Glioma, Childhood; Brain Tumor, Childhood (Other); Breast Cancer; Breast Cancer and Pregnancy; Breast Cancer, Childhood; Breast Cancer, Male; Bronchial Adenomas/Carcinoids, Childhood; Carcinoid Tumor, Childhood; Carcinoid Tumor, Gastrointestinal; Carcinoma, Adrenocortical; Carcinoma, Islet Cell; Carcinoma of Unknown Primary; Central Nervous System Lymphoma, Primary; Cerebellar Astrocytoma, Childhood; Cerebral Astrocytoma/Malignant Glioma, Childhood; Cervical Cancer; Childhood Cancers; Chronic Lymphocytic Leukemia; Chronic Myelogenous Leukemia; Chronic Myeloproliferative Disorders; Clear Cell Sarcoma of Tendon Sheaths; Colon Cancer; Colorectal Cancer, Childhood; Cutaneous T-Cell Lymphoma; Endometrial Cancer; Ependymoma, Childhood; Epithelial Cancer, Ovarian; Esophageal Cancer; Esophageal Cancer, Childhood; Ewing's Family of Tumors; Extracranial Germ Cell Tumor, Childhood; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastric (Stomach) Cancer, Childhood; Gastrointestinal Carcinoid Tumor; Germ Cell Tumor, Extracranial, Childhood; Germ Cell Tumor, Extragonadal; Germ Cell Tumor, Ovarian; Gestational Trophoblastic Tumor; Glioma, Childhood Brain Stem; Glioma, Childhood Visual Pathway and Hypothalamic; Hairy Cell Leukemia; Head and Neck Cancer; Hepatocellular (Liver) Cancer, Adult (Primary); Hepatocellular (Liver) Cancer, Childhood (Primary); Hodgkin's Lymphoma, Adult; Hodgkin's Lymphoma, Childhood; Hodgkin's Lymphoma During Pregnancy; Hypopharyngeal Cancer; Hypothalamic and Visual Pathway Glioma, Childhood; Intraocular Melanoma; Islet Cell Carcinoma (Endocrine Pancreas); Kaposi's Sarcoma; Kidney Cancer; Laryngeal Cancer; Laryngeal Cancer, Childhood; Leukemia, Acute Lymphoblastic, Adult; Leukemia, Acute Lymphoblastic, Childhood; Leukemia, Acute Myeloid, Adult; Leukemia, Acute Myeloid, Childhood; Leukemia, Chronic Lymphocytic; Leukemia, Chronic Myelogenous; Leukemia, Hairy Cell; Lip and Oral Cavity Cancer; Liver Cancer, Adult (Primary); Liver Cancer, Childhood (Primary); Lung Cancer, Non-Small Cell; Lung Cancer, Small Cell; Lymphoblastic Leukemia, Adult Acute; Lymphoblastic Leukemia, Childhood Acute; Lymphocytic Leukemia, Chronic; Lymphoma, AIDS-Related; Lymphoma, Central Nervous System (Primary); Lymphoma, Cutaneous T-Cell; Lymphoma, Hodgkin's, Adult; Lymphoma, Hodgkin's, Childhood; Lymphoma, Hodgkin's During Pregnancy; Lymphoma, Non-Hodgkin's, Adult; Lymphoma, Non-Hodgkin's, Childhood; Lymphoma, Non-Hodgkin's During Pregnancy; Lymphoma, Primary Central Nervous System; Macroglobulinemia, Waldenstrom's; Male Breast Cancer; Malignant Mesothelioma, Adult; Malignant Mesothelioma, Childhood; Malignant Thymoma; Medulloblastoma, Childhood; Melanoma; Melanoma, Intraocular; Merkel Cell Carcinoma; Mesothelioma, Malignant; Metastatic Squamous Neck Cancer with Occult Primary; Multiple Endocrine Neoplasia Syndrome, Childhood; Multiple Myeloma/Plasma Cell Neoplasm; Mycosis Fungoides; Myelodysplastic Syndromes; Myelogenous Leukemia, Chronic; Myeloid Leukemia, Childhood Acute; Myeloma, Multiple; Myeloproliferative Disorders, Chronic; Nasal Cavity and Paranasal Sinus Cancer; Nasopharyngeal Cancer; Nasopharyngeal Cancer, Childhood; Neuroblastoma; Non-Hodgkin's Lymphoma, Adult; Non-Hodgkin's Lymphoma, Childhood; Non-Hodgkin's Lymphoma During Pregnancy; Non-Small Cell Lung Cancer; Oral Cancer, Childhood; Oral Cavity and Lip Cancer; Oropharyngeal Cancer; Osteosarcoma/Malignant Fibrous Histiocytoma of Bone; Ovarian Cancer, Childhood; Ovarian Epithelial Cancer; Ovarian Germ Cell Tumor; Ovarian Low Malignant Potential Tumor; Pancreatic Cancer; Pancreatic Cancer, Childhood; Pancreatic Cancer, Islet Cell; Paranasal Sinus and Nasal Cavity Cancer; Parathyroid Cancer; Penile Cancer; Pheochromocytoma; Pineal and Supratentorial Primitive Neuroectodermal Tumors, Childhood; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Primary Liver Cancer, Adult; Primary Liver Cancer, Childhood; Prostate Cancer; Rectal Cancer; Renal Cell (Kidney) Cancer; Renal Cell Cancer, Childhood; Renal Pelvis and Ureter, Transitional Cell Cancer; Retinoblastoma; Rhabdomyosarcoma, Childhood; Salivary Gland Cancer; Salivary Gland Cancer, Childhood; Sarcoma, Ewing's Family of Tumors; Sarcoma, Kaposi's; Sarcoma (Osteosarcoma)/Malignant Fibrous Histiocytoma of Bone; Sarcoma, Rhabdomyosarcoma, Childhood; Sarcoma, Soft Tissue, Adult; Sarcoma, Soft Tissue, Childhood; Sezary Syndrome; Skin Cancer; Skin Cancer, Childhood; Skin Cancer (Melanoma); Skin Carcinoma, Merkel Cell; Small Cell Lung Cancer; Small Intestine Cancer; Soft Tissue Sarcoma, Adult; Soft Tissue Sarcoma, Childhood; Squamous Neck Cancer with Occult Primary, Metastatic; Stomach (Gastric) Cancer; Stomach (Gastric) Cancer, Childhood; Supratentorial Primitive Neuroectodermal Tumors, Childhood; T-Cell Lymphoma, Cutaneous; Testicular Cancer; Thymoma, Childhood; Thymoma, Malignant; Thyroid Cancer; Thyroid Cancer, Childhood; Transitional Cell Cancer of the Renal Pelvis and Ureter; Trophoblastic Tumor, Gestational; Unknown Primary Site, Cancer of, Childhood; Unusual Cancers of Childhood; Ureter and Renal Pelvis, Transitional Cell Cancer; Urethral Cancer; Uterine Sarcoma; Vaginal Cancer; Visual Pathway and Hypothalamic Glioma, Childhood; Vulvar Cancer; Waldenstrom's Macro globulinemia; and Wilms' Tumor. Metastases of the aforementioned cancers can also be treated or prevented in accordance with the methods described herein.

Cancer Combination Therapies

In some embodiments, a compound described herein is administered together with an additional cancer treatment. Exemplary cancer treatments include, for example: chemotherapy, targeted therapies such as antibody therapies, immunotherapy, and hormonal therapy. Examples of each of these treatments are provided below.

Chemotherapy

In some embodiments, a compound described herein is administered with a chemotherapy. Chemotherapy is the treatment of cancer with drugs that can destroy cancer cells. "Chemotherapy" usually refers to cytotoxic drugs which affect rapidly dividing cells in general, in contrast with targeted therapy. Chemotherapy drugs interfere with cell division in various possible ways, e.g., with the duplication of DNA or the separation of newly formed chromosomes. Most forms of chemotherapy target all rapidly dividing cells and are not specific for cancer cells, although some degree of specificity may come from the inability of many cancer cells to repair DNA damage, while normal cells generally can.

Examples of chemotherapeutic agents used in cancer therapy include, for example, antimetabolites (e.g., folic acid, purine, and pyrimidine derivatives) and alkylating agents (e.g., nitrogen mustards, nitrosoureas, platinum, alkyl sulfonates, hydrazines, triazenes, aziridines, spindle poison, cytotoxic agents, topoisomerase inhibitors and others). Exemplary agents include Aclarubicin, Actinomycin, Alitretinon, Altretamine, Aminopterin, Aminolevulinic acid, Amrubicin, Amsacrine, Anagrelide, Arsenic trioxide, Asparaginase, Atrasentan, Belotecan, Bexarotene, endamustine, Bleomycin, Bortezomib, Busulfan, Camptothecin, Capecitabine, Carboplatin, Carboquone, Carmofur, Carmustine, Celecoxib, Chlorambucil, Chlormethine, Cisplatin, Cladribine, Clofarabine, Crisantaspase, Cyclophosphamide, Cytarabine, Dacarbazine, Dactinomycin, Daunorubicin, Decitabine, Demecolcine, Docetaxel, Doxorubicin, Efaproxiral, Elesclomol, Elsamitrucin, Enocitabine, Epirubicin, Estramustine, Etoglucid, Etoposide, Floxuridine, Fludarabine, Fluorouracil (5FU), Fotemustine, Gemcitabine, Gliadel implants, Hydroxycarbamide, Hydroxyurea, Idarubicin, Ifosfamide, Irinotecan, Irofulven, Ixabepilone, Larotaxel, Leucovorin, Liposomal doxorubicin, Liposomal daunorubicin, Lonidamine, Lomustine, Lucanthone, Mannosulfan, Masoprocol, Melphalan, Mercaptopurine, Mesna, Methotrexate, Methyl aminolevulinate, Mitobronitol, Mitoguazone, Mitotane, Mitomycin, Mitoxantrone, Nedaplatin, Nimustine, Oblimersen, Omacetaxine, Ortataxel, Oxaliplatin, Paclitaxel, Pegaspargase, Pemetrexed, Pentostatin, Pirarubicin, Pixantrone, Plicamycin, Porfimer sodium, Prednimustine, Procarbazine, Raltitrexed, Ranimustine, Rubitecan, Sapacitabine, Semustine, Sitimagene ceradenovec, Strataplatin, Streptozocin, Talaporfin, Tegafur-uracil, Temoporfin, Temozolomide, Teniposide, Tesetaxel, Testolactone, Tetranitrate, Thiotepa, Tiazofurine, Tioguanine, Tipifarnib, Topotecan, Trabectedin, Triaziquone, Triethylenemelamine, Triplatin, Tretinoin, Treosulfan, Trofosfamide, Uramustine, Valrubicin, Verteporfin, Vinblastine, Vincristine, Vindesine, Vinflunine, Vinorelbine, Vorinostat, Zorubicin, and other cytostatic or cytotoxic agents described herein.

Because some drugs work better together than alone, two or more drugs are often given at the same time. Often, two or more chemotherapy agents are used as combination chemotherapy. In some embodiments, the chemotherapy agents (including combination chemotherapy) can be used in combination with a compound described herein.

Targeted Therapy

In some embodiments, a compound described herein is administered with a targeted therapy. Targeted therapy constitutes the use of agents specific for the deregulated proteins of cancer cells. Small molecule targeted therapy drugs are generally inhibitors of enzymatic domains on mutated, overexpressed, or otherwise critical proteins within the cancer cell. Prominent examples are the tyrosine kinase inhibitors such as Axitinib, Bosutinib, Cediranib, desatinib, erolotinib, imatinib, gefitinib, lapatinib, Lestaurtinib, Nilotinib, Semaxanib, Sorafenib, Sunitinib, and Vandetanib, and also cyclin-dependent kinase inhibitors such as Alvocidib and Seliciclib. Monoclonal antibody therapy is another strategy in which the therapeutic agent is an antibody which specifically binds to a protein on the surface of the cancer cells. Examples include the anti-HER2/neu antibody trastuzumab (HERCEPTIN®) typically used in breast cancer, and the anti-CD20 antibody rituximab and Tositumomab typically used in a variety of B-cell malignancies. Other exemplary antibodies include Cetuximab, Panitumumab, Trastuzumab, Alemtuzumab, Bevacizumab, Edrecolomab, and Gemtuzumab. Exemplary fusion proteins include Aflibercept and Denileukin diftitox. In some embodiments, the targeted therapy can be used in combination with a compound described herein.

Targeted therapy can also involve small peptides as "homing devices" which can bind to cell surface receptors or affected extracellular matrix surrounding the tumor. Radionuclides which are attached to these peptides (e.g., RGDs)

eventually kill the cancer cell if the nuclide decays in the vicinity of the cell. An example of such therapy includes BEXXAR®.

Immunotherapy

In some embodiments, a compound described herein is administered with an immunotherapy. Cancer immunotherapy refers to a diverse set of therapeutic strategies designed to induce the patient's own immune system to fight the tumor. Contemporary methods for generating an immune response against tumors include intravesicular BCG immunotherapy for superficial bladder cancer, and use of interferons and other cytokines to induce an immune response in renal cell carcinoma and melanoma patients.

Allogeneic hematopoietic stem cell transplantation can be considered a form of immunotherapy, since the donor's immune cells will often attack the tumor in a graft-versus-tumor effect. In some embodiments, the immunotherapy agents can be used in combination with a compound described herein.

Hormonal Therapy

In some embodiments, a compound described herein is administered with a hormonal therapy. The growth of some cancers can be inhibited by providing or blocking certain hormones. Common examples of hormone-sensitive tumors include certain types of breast and prostate cancers. Removing or blocking estrogen or testosterone is often an important additional treatment. In certain cancers, administration of hormone agonists, such as progestogens may be therapeutically beneficial. In some embodiments, the hormonal therapy agents can be used in combination with a compound described herein.

Obesity and Fat Disorders

A compound or composition described herein can be used to treat or prevent obesity, e.g., in a human subject, e.g. a child or adult subject. "Obesity" refers to a condition in which a subject has a body mass index of greater than or equal to 30. Many compounds described herein can be used to treat or prevent an over-weight condition. "Over-weight" refers to a condition in which a subject has a body mass index of greater or equal to 25.0. The body mass index (BMI) and other definitions are according to the "NIH Clinical Guidelines on the Identification and Evaluation, and Treatment of Overweight and Obesity in Adults" (1998). Treatment with the compound may be in an amount effective to alter the weight of the subject, e.g., by at least 2, 5, 7, 10, 12, 15, 20, 25, 30, 25, 40, 45, 50, or 55%. Treatment with a compound may be in an amount effective to reduce the body mass index of the subject, e.g., to less than 30, 28, 27, 25, 22, 20, or 18. The compounds can be used to treat or prevent aberrant or inappropriate weight gain, metabolic rate, or fat deposition, e.g., anorexia, bulimia, obesity, diabetes, or hyperlipidemia (e.g., elevated triglycerides and/or elevated cholesterol), as well as disorders of fat or lipid metabolism.

A compound or composition described herein can be administered to treat obesity associated with Prader-Willi Syndrome (PWS). PWS is a genetic disorder associated with obesity (e.g., morbid obesity).

A compound or composition described herein can be used to reduce body fat, prevent increased body fat, reduce cholesterol (e.g., total cholesterol and/or ratios of total cholesterol to HDL cholesterol), and/or reduce appetite in individuals having PWS associated obesity, and/or reduce comorbidities such as diabetes, cardiovascular disease, and stroke.

Compositions and Routes of Administration

The compositions delineated herein include the compounds delineated herein (e.g., a compound described herein), as well as additional therapeutic agents if present, in amounts effective for achieving a modulation of disease or disease symptoms, including those described herein.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compounds of the formulae described herein.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

When the compositions of this invention comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

The compounds described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.5 to about 100 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

Patient Selection and Monitoring

The compounds described herein can modulate PKM2. Accordingly, a patient and/or subject can be selected for treatment using a compound described herein by first evaluating the patient and/or subject to determine whether the subject is in need of modulation of PKM2, and if the subject is determined to be in need of modulation of PKM2, then optionally administering to the subject a compound described herein.

A subject can be evaluated as being in need of modulation of PKM2 using methods known in the art, e.g., by measuring the presence and/or activity of PKM2 in the patient. In some embodiments, the activity and/or level of PKM2 is evaluated in the cancer.

A patient receiving a compound described herein can be monitored, for example, for improvement in the condition and/or adverse effects. Improvement of a patient's condition can be evaluated, for example, by monitoring the growth, absence of growth, or regression of the cancer (e.g., a tumor). In some embodiments, the patient is evaluated using a radiological assay or evaluation of hemolytic parameters.

EXAMPLES

Example 1

PKM2 Assay

Procedure:
PKM2 stock enzyme solution was diluted in Reaction Buffer
2 μL of compound was added into each well first, and then 180 μL of the Reaction Mix was added.
Reaction mixture with compound (without ADP) were incubated for 30 minutes at 4° C.
Plates were re-equilibrated to room temperature prior to adding 20 μL ADP to initiate the reaction.
Reaction progress was measured as changes in absorbance at 340 nm wavelength at room temperature (25° C.)
Reaction Mix: PKM2 (50 ng/well), ADP (0.7 mM), PEP (0.15 mM), NADH (180 μM), LDH (2 units) in Reaction Buffer
Reaction Buffer: 100 mM KCl, 50 mM Tris pH 7.5, 5 mM MgCl2, 1 mM DTT, 0.03% BSA.
Results from this assay can be seen in Table 1.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

The invention claimed is:

1. A compound selected from formula (I):

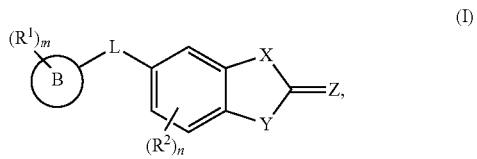

(I)

wherein:
m is an integer from 0 to 5;
each $R^1$ is independently selected from $C_1$-$C_6$ alkyl, $C_1$-$C_6$ alkoxy, $C_1$-$C_6$ haloalkyl, $C_{1-6}$ haloalkoxy, halo, acetyl, —$NO_2$, aryl, aralkyl, heteroaryl, —$SO_2$-aryl, —C(O)—$NR^b$-aryl, —C(O)-aralkyl, —C(O)—$C_{1-6}$ alkoxy, —$NR^b$—$SO_2$-aryl, wherein each aryl, aralkyl and heteroaryl group is optionally substituted with 0-3 occurrences of $R^c$ and wherein two $R^1$ groups taken together with the carbon atoms to which they are attached form a heterocyclyl ring;
n is an integer from 1 to 3;
each $R^2$ is independently selected from $C_1$-$C_6$ alkyl and halo;
B is aryl;
L is a linker selected from —$SO_2$—, —$SO_2NR^a$— and —$NR^aSO_2$—;
each $R^a$ is independently selected from hydrogen and $C_1$-$C_6$ alkyl;
wherein one of X and Y is O and the other is $NR^b$ or one of X and Y is S and the other is $NR^b$;
Z is O or S;
each $R^b$ is $C_1$-$C_6$ alkyl substituted with 0-1 occurrences of $R^c$; and $R^c$ is independently selected from $C_{1-6}$ alkyl, $C_{1-6}$ alkoxy, $C_{1-6}$ haloalkyl, halo, $NR^dR^d$, and heterocyclyl and wherein two $R^c$ groups taken together with the carbon atoms to which they are attached form a heterocyclyl ring; and
$R^d$ is independently selected from H and $C_{1-6}$ alkyl.

2. The compound of claim 1, wherein B is substituted with one $R^1$.

3. The compound of claim 1, wherein B is a monocyclic aryl.

4. The compound of claim 3, wherein B is substituted with one or two $R^1$.

5. The compound of claim 1, wherein n is 1.

6. The compound of claim 5, wherein the compound of formula (I) is represented by the following formula:

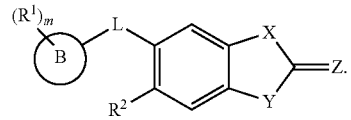

7. The compound of claim 1, wherein L is —SO—$NR^a$—.
8. The compound of claim 7, wherein $R^a$ is H.
9. The compound of claim 1, wherein L is —$SO_2$—.
10. The compound of claim 1, wherein each $R^1$ is independently selected from $C_{1-6}$ alkyl, $C_{1-6}$ alkoxy, $C_{1-6}$ haloalkyl, halo, acetyl and —$NO_2$.
11. The compound of claim 1, wherein Z is O.
12. The compound of claim 1, wherein one of X and Y is O and the other is $NR^b$.
13. The compound of claim 1, wherein one of X and Y is S and the other is $NR^b$.
14. A compound selected from formula (III):

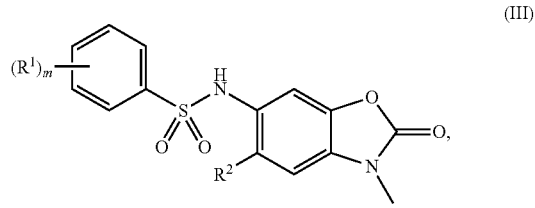

(III)

wherein:
m is an integer from 0 to 5;
each $R^1$ is independently selected from $C_1$-$C_6$ alkyl, $C_1$-$C_6$ alkoxy, $C_1$-$C_6$ haloalkyl, $C_{1-6}$ haloalkoxy, halo, acetyl, —$NO_2$, aryl, aralkyl, heteroaryl, —$SO_2$-aryl, —C(O)—$NR^b$-aryl, —C(O)-aralkyl, —C(O)—$C_{1-6}$ alkoxy, —$NR^b$—$SO_2$-aryl, wherein each aryl, aralkyl and heteroaryl group is optionally substituted with 0-3 occurrences of $R^c$ and wherein two $R^1$ groups taken together with the carbon atoms to which they are attached form a heterocyclyl ring;
each $R^2$ is independently selected from $C_1$-$C_6$ alkyl and halo;
each $R^b$ is independently selected from hydrogen, $C_{1-6}$ aralkyl, and $C_1$-$C_6$ alkyl substituted with 0-1 occurrences of $R^c$;
$R^c$ is independently selected from $C_{1-6}$ alkyl, $C_{1-6}$ alkoxy, $C_{1-6}$ haloalkyl, halo, $NR^dR^d$, and heterocyclyl and wherein two $R^c$ groups taken together with the carbon atoms to which they are attached form a heterocyclyl ring; and
$R^d$ is independently selected from H and $C_{1-6}$ alkyl.

15. The compound of claim 14, wherein m is 0.

16. The compound of claim 14, wherein m is 1 or 2.

17. The compound of claim 14, wherein each $R^1$ is independently selected from $C_{1-6}$ alkyl, $C_{1-6}$ alkoxy, $C_{1-6}$ haloalkyl, halo, acetyl and $-NO_2$.

18. The compound of claim 14, wherein $R^2$ is methyl.

* * * * *